(12) United States Patent
Bierman

(10) Patent No.: US 7,785,295 B2
(45) Date of Patent: *Aug. 31, 2010

(54) MEDICAL LINE SECUREMENT DEVICE

(75) Inventor: Steven F. Bierman, Del Mar, CA (US)

(73) Assignee: Venetec International, Inc., Covington, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/837,483

(22) Filed: Aug. 10, 2007

(65) Prior Publication Data

US 2007/0276332 A1 Nov. 29, 2007

Related U.S. Application Data

(63) Continuation of application No. 11/527,904, filed on Sep. 26, 2006, now Pat. No. 7,635,355, which is a continuation of application No. 10/429,217, filed on May 1, 2003, now Pat. No. 7,223,256.

(60) Provisional application No. 60/377,060, filed on May 1, 2002, provisional application No. 60/381,728, filed on May 17, 2002, provisional application No. 60/400,579, filed on Jul. 31, 2002, provisional application No. 60/400,638, filed on Jul. 31, 2002.

(51) Int. Cl.
*A61M 5/32* (2006.01)

(52) U.S. Cl. ............... 604/180; 604/174

(58) Field of Classification Search ......... 604/175–180, 604/174; 128/DIG. 6, DIG. 26
See application file for complete search history.

(56) References Cited

U.S. PATENT DOCUMENTS

| 3,766,915 | A | 10/1973 | Rychlik |
| 3,896,527 | A | 7/1975 | Miller et al. |
| 3,942,228 | A | 3/1976 | Buckman et al. |
| 3,993,081 | A | 11/1976 | Cussell |
| 4,082,094 | A | 4/1978 | Dailey |

(Continued)

FOREIGN PATENT DOCUMENTS

EP 0 567 029 A1 10/1993

(Continued)

*Primary Examiner*—Kevin C Sirmons
*Assistant Examiner*—Laura C Schell
(74) *Attorney, Agent, or Firm*—Knobbe Martens Olson & Bear LLP

(57) ABSTRACT

A medical line securement device holds a medical article such as a connector fitting for a catheter or a catheter adaptor in position upon the body of a patient and inhibits axial motion of the medical article. The securement device includes a retainer with a base and a cover. The cover is hinged to the base such that it may be moved between an open and closed position. The base and cover each have a groove which cooperate when the cover is in the closed position to form a channel through the retainer. The medical article includes an elongated body which is received within the groove of the retainer, the elongated body lying between at least a pair of regions of larger radius of the medical article. By receiving the portion of the elongated body of the medical article between the regions of larger radius, axial motion of the medical article through the groove is inhibited. The retainer may also include one or more slots to receive any radial projections of the medical article within the retainer.

13 Claims, 13 Drawing Sheets

U.S. PATENT DOCUMENTS

| | | | |
|---|---|---|---|
| 4,193,174 A | | 3/1980 | Stephens |
| 4,209,015 A | | 6/1980 | Wicks |
| 4,224,937 A | * | 9/1980 | Gordon ..................... 604/180 |
| 4,250,880 A | | 2/1981 | Gordon |
| 4,356,599 A | | 11/1982 | Larson et al. |
| 4,397,647 A | | 8/1983 | Gordon |
| 4,402,691 A | * | 9/1983 | Rosenthal et al. ........... 604/411 |
| 4,405,312 A | * | 9/1983 | Gross et al. .................... 604/29 |
| 4,484,913 A | | 11/1984 | Swauger |
| 4,498,903 A | | 2/1985 | Mathew |
| 4,623,102 A | | 11/1986 | Hough, Jr. |
| 4,711,636 A | | 12/1987 | Bierman |
| 4,775,121 A | | 10/1988 | Carty |
| 4,857,058 A | | 8/1989 | Payton |
| 4,863,432 A | | 9/1989 | Kvalo |
| 4,897,082 A | | 1/1990 | Erskine |
| 4,898,587 A | | 2/1990 | Mera |
| 4,955,864 A | | 9/1990 | Hajduch |
| 4,976,700 A | | 12/1990 | Tollini |
| 4,997,421 A | | 3/1991 | Palsrok et al. |
| 5,037,397 A | | 8/1991 | Kalt et al. |
| 5,098,399 A | | 3/1992 | Tollini |
| 5,192,273 A | | 3/1993 | Bierman et al. |
| 5,195,981 A | | 3/1993 | Johnson |
| 5,226,892 A | | 7/1993 | Boswell |
| 5,248,306 A | | 9/1993 | Clark et al. |
| 5,263,943 A | | 11/1993 | Vanderbrook |
| 5,314,411 A | | 5/1994 | Bierman et al. |
| 5,334,186 A | | 8/1994 | Alexander |
| 5,354,282 A | | 10/1994 | Bierman |
| 5,368,575 A | | 11/1994 | Chang |
| 5,382,239 A | | 1/1995 | Orr et al. |
| 5,389,082 A | | 2/1995 | Baugues et al. |
| 5,398,679 A | | 3/1995 | Freed |
| 5,431,695 A | | 7/1995 | Wiklund et al. |
| 5,456,671 A | | 10/1995 | Bierman |
| 5,494,245 A | | 2/1996 | Suzuki et al. |
| 5,499,976 A | | 3/1996 | Dalton |
| 5,578,013 A | | 11/1996 | Bierman |
| 5,681,290 A | | 10/1997 | Alexander |
| 5,685,859 A | | 11/1997 | Kornerup |
| 5,755,225 A | | 5/1998 | Hutson |
| 5,800,402 A | | 9/1998 | Bierman |
| 5,810,781 A | | 9/1998 | Bierman |
| 5,827,230 A | * | 10/1998 | Bierman ..................... 604/174 |
| 5,827,239 A | | 10/1998 | Dillon et al. |
| 5,846,255 A | | 12/1998 | Casey |
| 5,916,199 A | | 6/1999 | Miles |
| 5,944,696 A | | 8/1999 | Bayless et al. |
| 6,001,081 A | | 12/1999 | Collen |
| 6,015,119 A | | 1/2000 | Starchevich |
| 6,206,897 B1 | | 3/2001 | Jamiolkowski et al. |
| 6,213,979 B1 | | 4/2001 | Bierman |
| 6,283,945 B1 | | 9/2001 | Bierman |
| 6,290,676 B1 | | 9/2001 | Bierman |
| 6,311,933 B1 | | 11/2001 | Starchevich |
| 6,361,523 B1 | | 3/2002 | Bierman |
| 6,387,076 B1 | | 5/2002 | Landuyt |
| 6,447,486 B1 | | 9/2002 | Tollini |
| 6,458,104 B2 | | 10/2002 | Gautsche |
| 6,482,183 B1 | | 11/2002 | Pausch et al. |
| 6,572,587 B2 | | 6/2003 | Lehrman et al. |
| 6,572,588 B1 | | 6/2003 | Bierman et al. |
| 6,631,715 B2 | | 10/2003 | Kirn |

FOREIGN PATENT DOCUMENTS

| | | |
|---|---|---|
| WO | WO 99/55409 | 11/1999 |

* cited by examiner

MEDICAL LINE SECUREMENT DEVICE

RELATED APPLICATIONS

This application is a continuation of U.S. application Ser. No. 11/527,904, filed on Sep. 26, 2006, entitled MEDICAL LINE SECUREMENT DEVICE, issued as U.S. Pat. No. 7,635,355, which is a continuation of U.S. application Ser. No. 10/429,217, filed on May 1, 2003, entitled MEDICAL LINE SECUREMENT DEVICE, issued as U.S. Pat. No. 7,223,256, which claims priority under 35 U.S.C. §119(e) from Provisional Application No. 60/377,060, filed on May 1, 2002, Provisional Application No. 60/381,728, filed May 17, 2002, Provisional Application No. 60/400,579, filed on Jul. 31, 2002, and Provisional Application No. 60/400,638, filed on Jul. 31, 2002, the entirety of each of which is hereby incorporated by reference herein.

BACKGROUND OF THE INVENTION

1. Field of the Invention

This invention relates to a escapement device for use with medical articles. More specifically, this invention relates to an anchoring system which releasably retains a fitting or adaptor of the medical article in position upon a patient.

2. Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical line properly positioned for the duration of treatment, the catheter or medical line may be secured to the patient in a variety of ways. Most commonly, this involves taping the catheter or medical line to the patient.

Securing a catheter with tape upon the patient traditionally has certain drawbacks. The use of tape at the insertion site may retain dirt or other contaminant particles, potentially leading to infection of the patient. Additionally, removal of taped dressings may itself cause undesired motion of the catheter upon the patient.

Taped dressings also require periodic changes. The frequent, often daily, removal and reapplication of adhesive tape to the skin of the patient can excoriate the skin in the area around the dressing. Such repeated applications of tape over the catheter or medical line may additionally lead to the build up of adhesive residue on the outer surface of the catheter or medical line. This residue can result in contaminants adhering to the catheter itself, increasing the likelihood of infection of the insertion site. This residue may also make the catheter or medical line stickier and more difficult to handle for medical attendants.

For these reasons, a need exists for an improved way to secure catheters and medical lines to patients where the catheter may remain in place over an extended period of time and may be easily released from the securement device.

SUMMARY OF THE INVENTION

In accordance with one aspect of the systems and techniques described herein, a releasable medical line securement system is provided. The system includes a retainer comprising a body made up of a base and a cover. The base and cover are movable with respect to each another, and may be moved so as to establish a closed condition and an open condition. When in the closed condition, the base and cover cooperate to form a channel. The body of the retainer has at least one surface which extends in a direction normal to the axis of the channel.

The system also can include a medical article which has an elongated body and at least one radially expending member that extends from the elongated body in a direction normal to the axis of the elongated body. The radially extending member of the medical article abuts the surface of the retainer when the retainer is in the closed condition, in order to inhibit longitudinal motion of the medical article through the retainer In another aspect, a retainer is provided for releasably securing a fitting for an elongated medical article. The fitting defines a maximum radial dimension from an axial centerline of the elongated medical article. The retainer comprises a body, comprising a base and a cover. The base and cover are movable as described above in order to establish a closed configuration and an open configuration. The base has a first groove and the cover has a second groove, the first and second grooves arranged so that when the base and cover are in the closed configuration the grooves define a channel with a central axis. The channel defines a minimum radial dimension from an axial centerline of the channel and this minimum radial dimension of the channel is smaller than the maximum lateral dimension of the fitting.

In accordance with another aspect of the systems and techniques described herein, a system for releasably securing a medical line or catheter is provided. The medical line or other medical article to be secured may include an elongated body, a radially extending member having a radius greater than the elongated body, and a spin nut for attaching the medical line to a second medical line. A retainer for the medical line is provided which includes a base and a cover which are coupled together and are movable between an open position and a closed position. When the cover is moved in the closed position, a channel is defined between the base and the cover, the channel being configured to receive at least a portion of the elongated body of the medical article. The retainer inhibits axial movement of the medical article through the channel when the cover is placed in a closed position.

In an alternative aspect, the medical line may include a second region with a radius greater than the elongated body of the medical line.

In a further aspect of a system in accordance with the description herein, the portion of the medical article which is received by the channel of the retainer is located between the radially extending member and the spin nut or another radially extending member of the medical article.

In another aspect of a system in accordance with the description herein, one or more slots may be disposed transverse to the axis of the groove. These slots may be configured to receive a tab or other projection located upon the medical line, such as the tab of a catheter adaptor.

In another aspect the retainer further comprises a latching mechanism which operates between the base and the cover to selectively secure the cover to the base when the cover is in the closed position. The latching mechanism may include an arm, an actuator bar attached to the arm, and a button disposed on the end of the actuator bar. The arm may be flexibly connected to the base of the retainer, and may include a pair of tangs at the upper end of the arm. Lateral pressure upon the button may deflect the arm such that the tangs are moved laterally.

In a further aspect of the described system, the cover of the retainer may include a pair of receiver openings into which the tangs are positioned when the cover is in the closed position. The tangs are deflected laterally via the button and actuator bar and arm in order to release the tangs from the receiver openings and release the cover from the closed position.

In another aspect of the described system the base of the retainer may include a lower groove and the cover of the retainer may include an upper groove. The upper groove and lower groove may cooperate to form the channel of the retainer when the cover is in the closed position.

In yet another aspect of the described system, a set of projections may be disposed adjacent to either the upper groove or lower groove of the retainer, the set of projections extending vertically from the edge of the groove. The projections may form an extension of the surface of the groove to which the projections are disposed, such that the groove surrounds the axis of the groove through an arc of greater than 180°. This may be used to provide a snap-fit securement between the medical article and the retainer.

Another aspect of a technique in accordance with the system described herein is a method for releasably securing a medical article to a retainer. This method may include providing a medical article in accordance with any of the aspects described above, and providing a retainer in accordance with any of the aspects described above. The cover of the retainer may be placed in the open position, and the medical article attached to the retainer by placing the elongated or tubular region of the medical article into the lower groove of the retainer. The cover of the retainer may then be placed into the closed position.

In a further aspect of a technique as described herein, the cover may be secured into the closed position by a latching mechanism in accordance with any of the aspects described herein.

For purposes of summarizing, certain aspects, advantages and novel features have been described herein. It is to be understood that not necessarily all such advantages may be achieved in accordance with any particular embodiment. Thus, the systems described may be embodied or carried out in a manner that achieves or optimizes one advantage or group of advantages as taught herein without necessarily achieving other advantages as may be taught or suggested herein.

BRIEF DESCRIPTION OF THE DRAWINGS

The above mentioned and other features will now be described with reference to the drawings of the present securement system. The shown embodiments are intended to illustrate, but not to limit the invention. The drawings contain the following figures.

DETAILED DESCRIPTION OF THE PREFERRED EMBODIMENTS

The following description and Figures describing various preferred embodiments are made to demonstrate various configurations of possible systems in accordance with the current invention. The embodiments illustrated are shown in use with a variety of exemplary connector fittings that can include a spin nut for connection to a catheter adaptor. This is not intended to limit the disclosed concepts to the specified embodiments or to usage with the illustrated connector fittings or catheter adaptors only. In addition, various systems will be described in the context of an exemplary securement device incorporating the described systems and techniques. Those of skill in the art will recognize that the techniques described are neither limited to any particular type of securement device, nor to the securement of any particular type of medical article for every described aspect herein.

Figure 1:
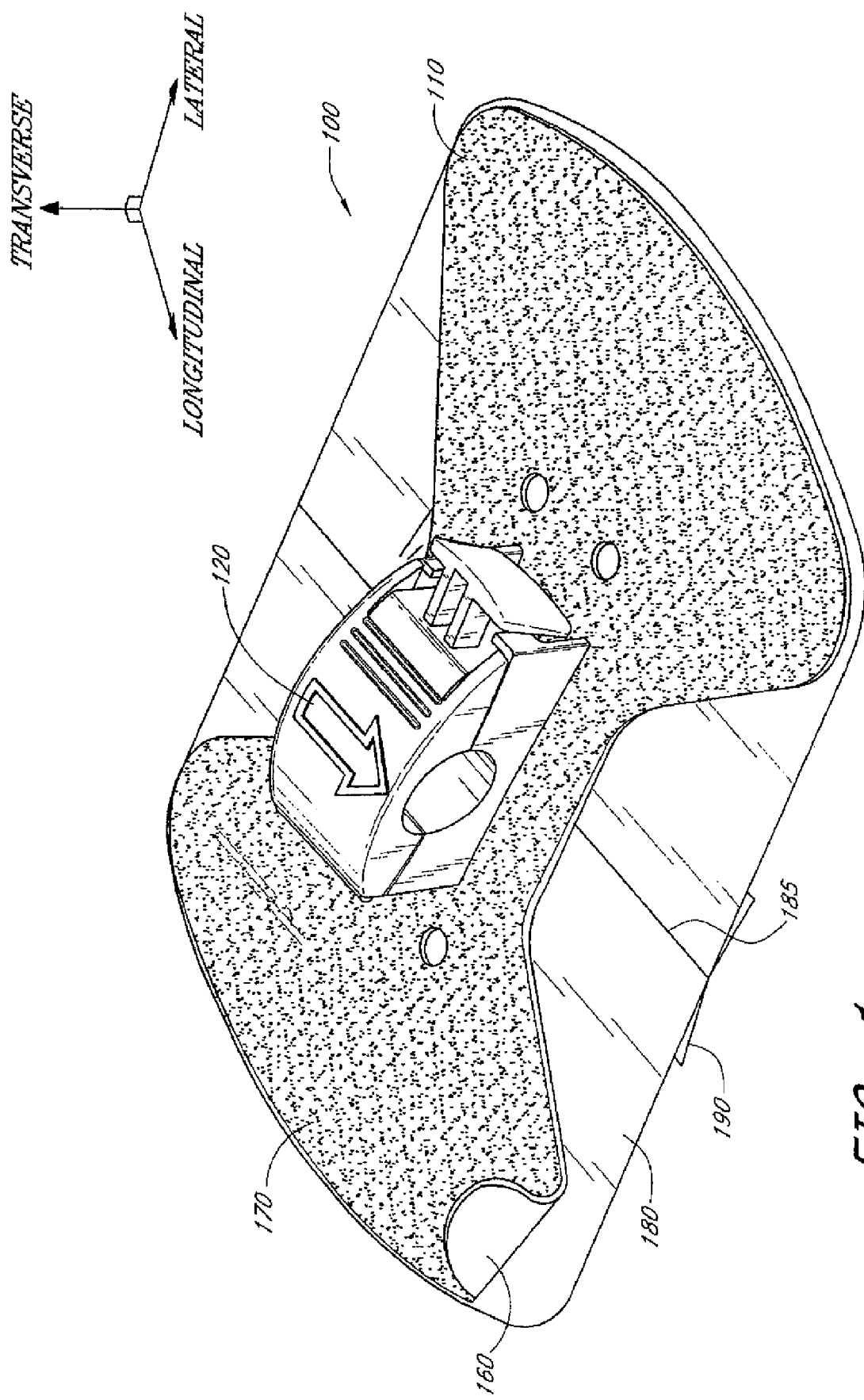
FIG. 1 illustrates a perspective view of one embodiment of a medical line securement device in accordance with the disclosure herein.

To assist in the description of these components of the anchoring system (see FIG. 1), the following coordinate terms are used. A "longitudinal axis" is generally parallel to the portion of the connector fitting or other medical article retained by the securement system, as well as parallel to the axis of the channel of the retainer. A "lateral axis" is normal to the longitudinal axis and is generally parallel to the plane of an anchor pad, as seen in FIG. 1. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of a channel or connector fitting, and therefore is substantially synonymous with the term "longitudinal" as used herein. The term "radial" refers to any direction which is normal to the axial direction, and may include both the transverse and lateral directions, as well as directions having both a lateral and a transverse component. Also, the terms "proximal" and "distal", which are used to describe the present anchoring system, are used consistently with the description of the exemplary applications. Thus, proximal and distal are used in reference to the center of the patient's body. The terms "upper," "lower," "top," "bottom,"

and the like, which also are used to describe the present anchoring system, are used in reference to the illustrated orientation of the embodiment.

To facilitate a complete understanding of the invention, the remainder of the detailed description describes the invention with reference to the Figures, wherein like elements are referenced with like numerals throughout.

Overview

Prior to describing particular embodiments of the illustrated medical line securement systems, a brief overview explaining the major components of the system and its use will be presented. As shown by the exemplary medical line securement system of FIG. 1, the system can comprise a securement device 100 in two main components: an anchor pad 110 and a retainer 120. As noted above and discussed in greater detail below, the securement device 100 can form a component of a catheterization system that also includes one or more medical articles, such as connector fittings, catheter adaptors, fluid supply lines, or other articles suitable for securement via the anchor pad 110 and retainer 120.

Figure 2:
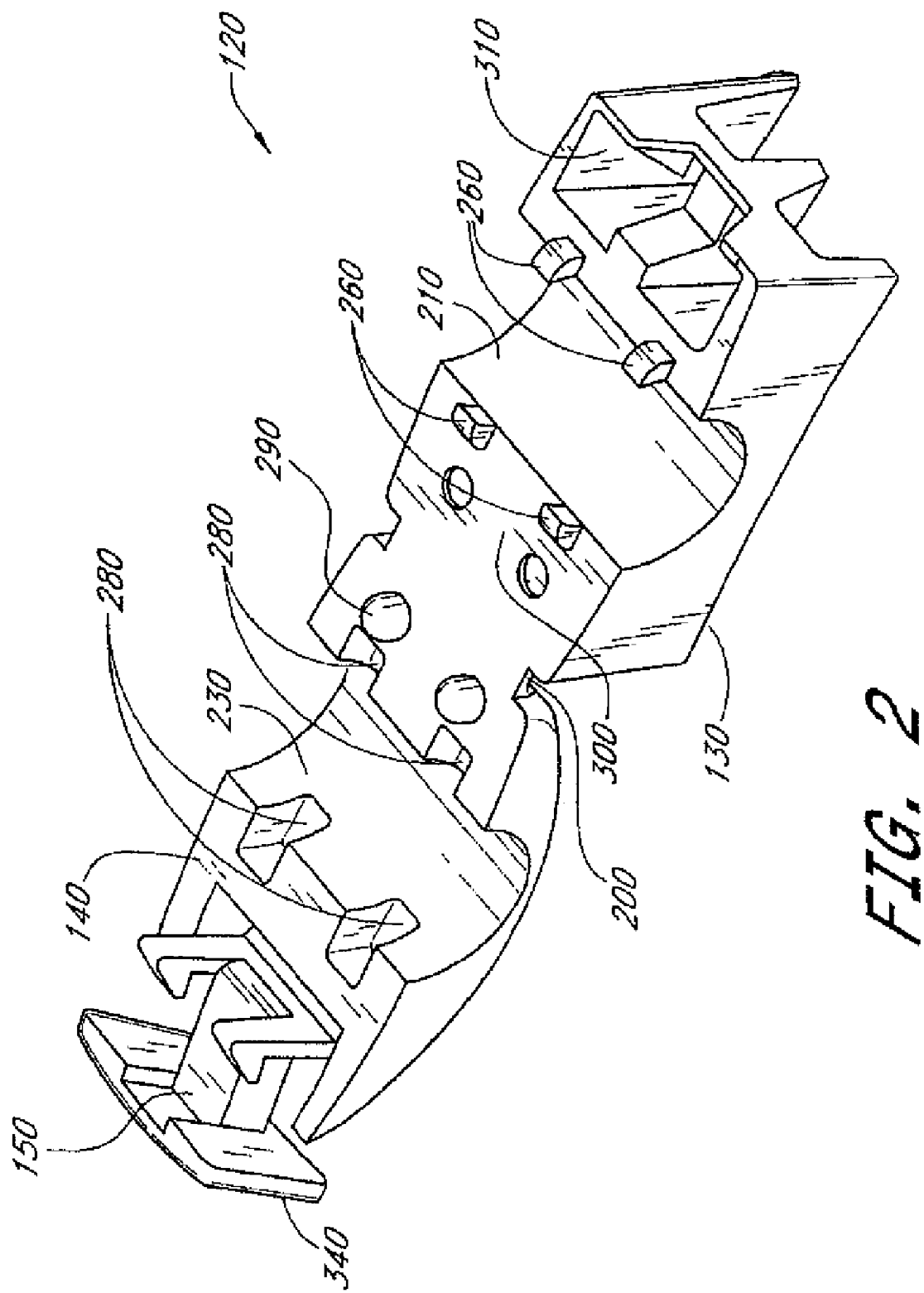
FIG. 2 illustrates a perspective view of the retainer of FIG. 1 in an open condition.

The retainer 120 is mounted upon the anchor pad 110 and the anchor pad is secured to the skin of a patient, generally by an adhesive disposed upon the bottom surface of the pad. The retainer is configured to receive a medical article and secure it in position. An exemplary retainer 120, as shown in FIG. 2, can comprise several sub-components, including a base 130, a cover 140, and a latch 150 for securing the cover of the retainer over the base in a closed condition. The releasable engagement of a medical article is achieved, at least in part, by cooperation between the base 130 and the cover 140 in forming a channel through the retainer 120. Because the cover may be opened after the medical article is secured, it is possible for the medical article to be removed from the securement device 100 for any necessary purpose. This can include purposes such as replacing the securement device, replacing the medical line, or moving the patient. This removal of the medical article from the securement device can be accomplished without removing the device from the patient if desired.

Figure 9A:
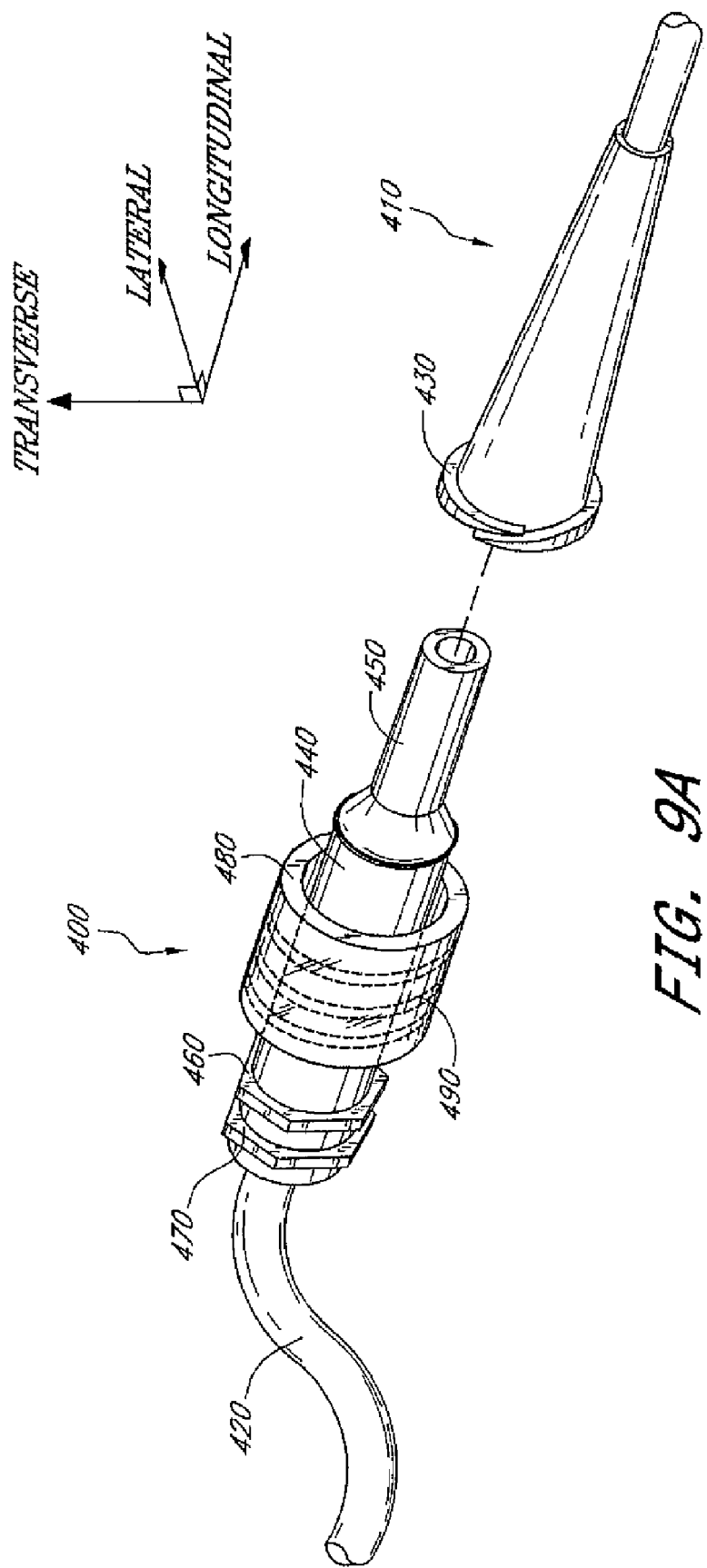
FIG. 9A illustrates a perspective view of a connector fitting with a spin nut for use with the retainer of FIG. 2.

A medical article, for instance the exemplary connector fitting 400 illustrated in FIG. 9A, can be held in position through a combination of lateral and transverse pressure along the secured portion of the medical article within a channel of the retainer 120. In the illustrated embodiment of FIG. 9A, the connector fitting 400 includes a spin nut 480 that can be used to secure a catheter hub 410 to the connector fitting, as will be discussed in greater detail below.

In general, the retainer 120 can be used to hold the connector fitting 400 or the catheter hub 410 at any point along the combination of the two. Particular examples will be provided in the description which follows. As illustrated in FIG. 2, the retainer 120 generally includes a channel formed between grooves disposed upon the base 130 and the cover 140 of the retainer. Pressure is provided by the walls of the channel and the medical article is held within these walls when the retainer's cover is placed in a closed condition. In addition, if the connector fitting is of a generally rigid nature, a degree of snap fit may be provided between the retainer and the connector fitting by extending the walls of the groove in the base of the retainer around the axis of the channel at least partially through an arc of greater than 180°.

When the cover 140 is secured by the latch 150, the retainer is in a closed condition, as shown in FIG. 1. In this condition, the medical article is inhibited from moving substantially in either the lateral or transverse directions. Longitudinal motion of the medical article is inhibited by the positioning of the connector fitting or other article upon the retainer 120 such that portions of the medical article of larger radius than at least a portion of the channel are located adjacent to portions of the retainer having a smaller radius. This can be provided in various ways as will be described for each of the illustrated embodiments below.

The securement device 100 also desirably releasably engages the connector fitting or other medical article. This allows the securement device to be disengaged from the connector fitting without removing the medical article from the patient for any of a variety of known purposes. For instance, the healthcare provider may wish to remove the securement device in order to change the anchor pad 110 or to clean the insertion site without removing the catheter and its associated fitting from the patient. In situations where a catheter is in position in the patient for an extended period of time, it is advantageous to periodically change the securement device in order to maintain the best positional securement of the catheter. For these purposes, it is desirable that the disengagement of the medical article from the securement device can be accomplished without removing the medical article from the patient.

Retainer with Channel

One particular embodiment of a medical line securement system will now be described with reference to FIGS. 1 to 8. As shown in FIG. 1, one embodiment of the securement system 100 comprises a retainer 120 which is disposed upon an anchor pad 110. The anchor pad 110 desirably comprises a laminate structure with an upper woven layer and a lower adhesive layer. The upper layer may be polyester or other suitable polymer or textile materials. One particular suitable material is a woven polyester available commercially under the name "Tricot" from Tyco. The lower adhesive layer constitutes the lower surface 160 of the anchor pad. The lower surface desirably is a medical-grade adhesive and can be either diaphoretic or nondiaphoretic, depending upon the particular application. The anchor pad 110 can include suture holes in addition to the adhesive layer to further secure the anchor pad to the patient's skin.

In another embodiment, a hydrocolloid adhesive may advantageously be used upon the anchor pad 110 for attaching the anchor pad to the skin of the patient. The hydrocolloid adhesive can be used either alone or in combination with another medical grade adhesive (e.g., in combination with the adhesive available from Avery Dennison). The hydrocolloid adhesive has less of a tendency to excoriate the skin of a patient when removed. This may be particularly important for patients whose skin is more sensitive or fragile, such as those with a collagen deficiency or other skin related condition.

A surface of the upper foam layer constitutes an upper surface 170 of the anchor pad. The upper surface can be roughened by corona-treating the foam with a low electric charge. The roughened or porous upper surface can improve the quality of the adhesive joint (which is described below) between the base 130 and the anchor pad 110. In the alternative, the flexible anchor pad can comprise a medical-grade adhesive lower layer, an inner foam layer and an upper paper or other woven or nonwoven cloth layer.

A removable paper or plastic release liner 180 desirably covers the adhesive lower surface 160 before use. The liner 180 preferably resists tearing and desirably is divided into a plurality of pieces to ease attachment of the pad to a patient's skin. In the illustrated embodiment, the liner 180 is split along a center line 185 of the flexible anchor pad in order to expose only half of the adhesive lower surface 160 at one time.

The liner length, as measured in the lateral direction, extends beyond the center line 185 of the anchor pad 110 and is folded over, or back onto the liner. This folded over portion defines a pull tab 190 to facilitate removal of the liner 180 from the adhesive lower surface 160. A medical attendant uses the pull tab 190 by grasping and pulling on it so that the liner 180 is separated from the lower surface 160. The pull tab 190 overcomes any requirement that the medical attendant pick at a corner edge or other segment of the liner in order to separate the liner from the adhesive layer. The pull tab of course can be designed in a variety of configurations. For example, the pull tab can need not be located along a center line 185 of the anchor pad; rather, the pull tab can be located along any line of the anchor pad in order to ease the application of the anchor pad onto the patient's skin at a specific site. For example, an area of a patient's skin with an abrupt bend, such as at a joint, can require that the pull tab be aligned toward one of the lateral ends of the anchor pad rather than along the center line.

Figure 1A:
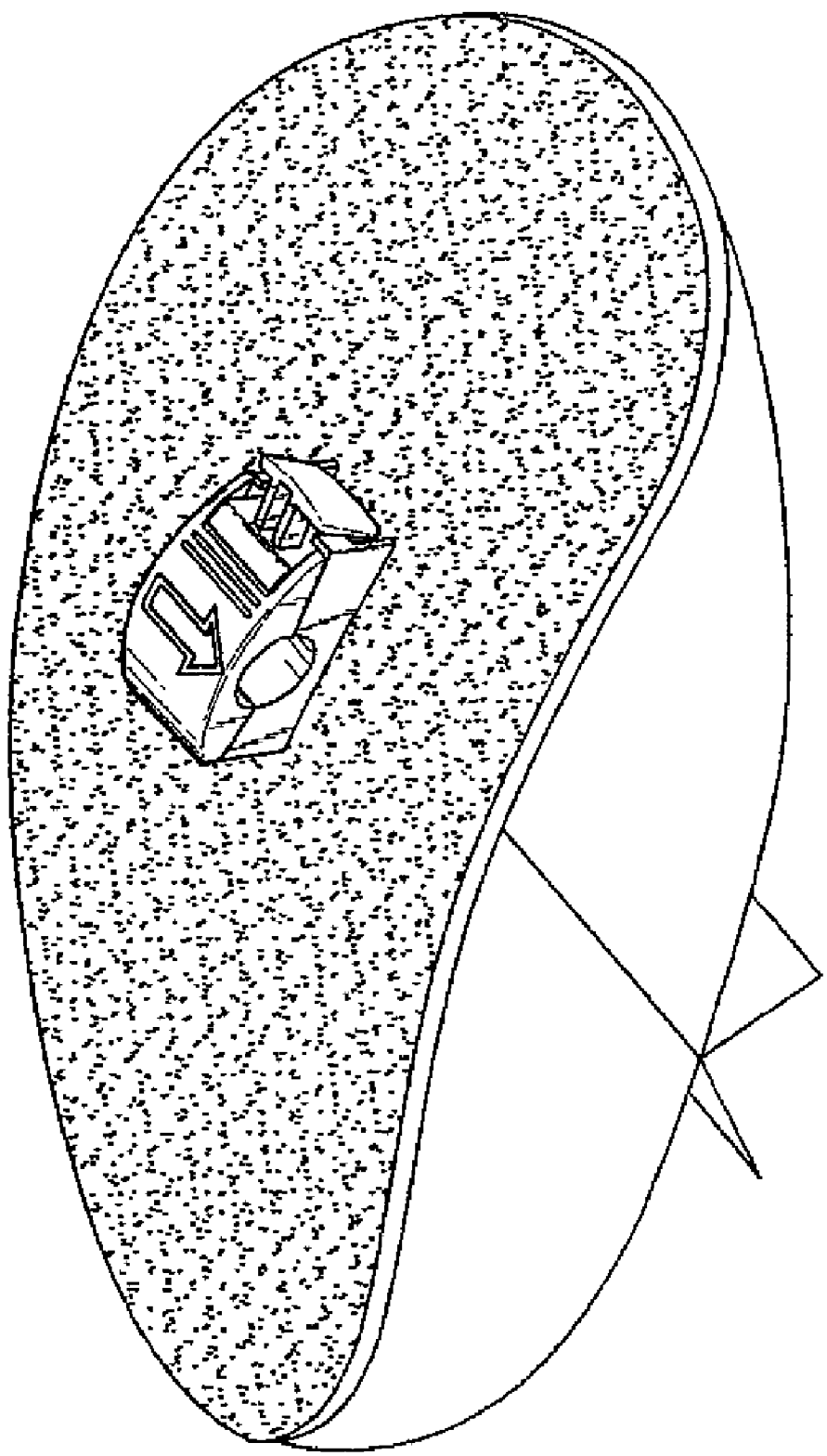
FIG. 1A illustrates a perspective view of another embodiment of a medical line securement device in accordance with the disclosure herein.

As best seen in FIG. 1, the anchor pad 110 also desirably includes a pair of opposing concave sections that narrows the center of the anchor pad proximate to the retainer 120. As a result, the lateral sides of the anchor pad have more contact area which provides greater stability and adhesion to a patient's skin. Although only a single shape of anchor pad is illustrated in FIG. 1, those of skill in the art will recognize that a variety of shapes may be used in various circumstances in order to most effectively attach the securement device to a patient. For instance, an alternate shape for an anchor pad for use with the embodiment of the retainer described below is shown in FIG. 1A. Through the use of such variations in the shape, material, and adhesive of the anchor pad, an appropriate base for anchoring a retainer may be provided for a variety of locations on the skin of a patient.

Retainer

With reference now to FIGS. 1 to 5, the retainer 120 includes a rigid structure principally formed by a first portion and a second portion which are movably attached so as to define open and closed conditions for the retainer 120. In the illustrated embodiment, the first portion is shown as a base 130 of the retainer, while the second portion is shown as a cover 140 (see FIG. 2). As shown in the FIGURES, base 130 and cover 140 are integrally formed to comprise a unitary retainer 120. This can be accomplished in any of a variety of ways well known to those skilled in the art. For instance, the entire retainer can be injection molded in order to reduce fabrication costs. The base 130 and cover 140, however, can be formed separately and then coupled together.

As mentioned above, the first and second portions together generally cooperate to define an open condition and a closed condition for the retainer 120. In the open condition, the retainer is able to receive a medical article, such as a connector fitting 400 (described below), within a portion of the retainer 120. In the closed condition, the retainer 120 inhibits motion of the received portion of the medical article relative to the retainer 120 as will be further discussed. The relative motion of the first and second portions of the retainer may be accomplished by a variety of means, such as pin-and-receiver hinges, flexible connections, rotatable connections, or any of a variety of other connectors which provide for relative motion between the first and second portions of the retainer 120. In the retainer illustrated in FIGS. 1 and 2, the connection between the first and second portions of the retainer 120 is a hinge formed from a flexible connecting piece.

As will be apparent from the below description, several features of the illustrated retainer 120, such as the latch 150 and hinge 200, are desirably flexible. Suitable rigid but flexible materials include, for example but without limitation: plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. The illustrated retainer 120 preferably is formed by injection molding using polyethylene or polypropylene material. However, other materials can be utilized, and the retainer can comprise a non-unitary base and cover.

As is illustrated in FIGS. 1 and 2, one retainer 120 may comprise an elongated body of a generally parallelepiped shape. The illustrated retainer includes a flexible hinge 200 at one lateral end of the body. The hinge 200 joins the base 130 of the retainer to the cover 140. The base 120 of the retainer, as illustrated more clearly in FIGS. 2 and 3, has a pair of opposing longitudinal sides, and a pair of lateral ends. The hinge 200 is disposed upon one lateral end, and a latch 150 is disposed upon the other lateral end. The upper side of the base 130 faces away from the anchor pad 110 and can desirably comprise a groove 210 that extends along the upper surface of the base 130 in a longitudinal direction. The lower side of the base 130 may be attached to the anchor pad 110 using a variety of means as are known in the art.

Figure 5:
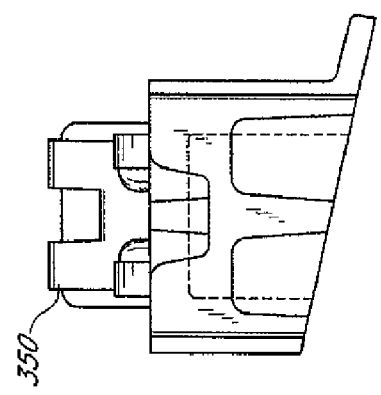
FIG. 5 illustrates a side view of the retainer of FIG. 2.
Figure 3:
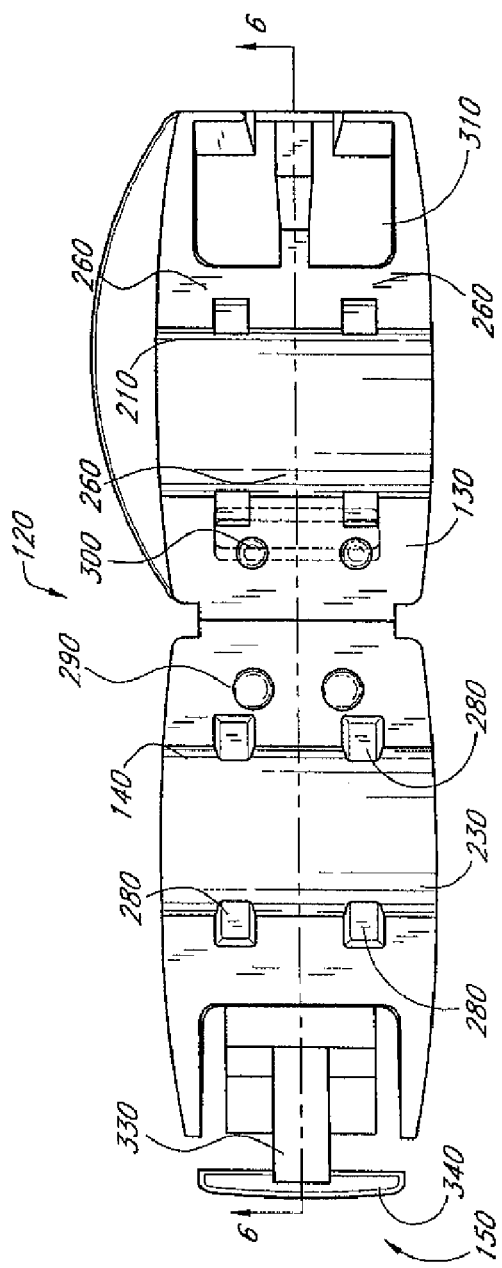
FIG. 3 illustrates a top view of the retainer of FIG. 2.
Figure 4:
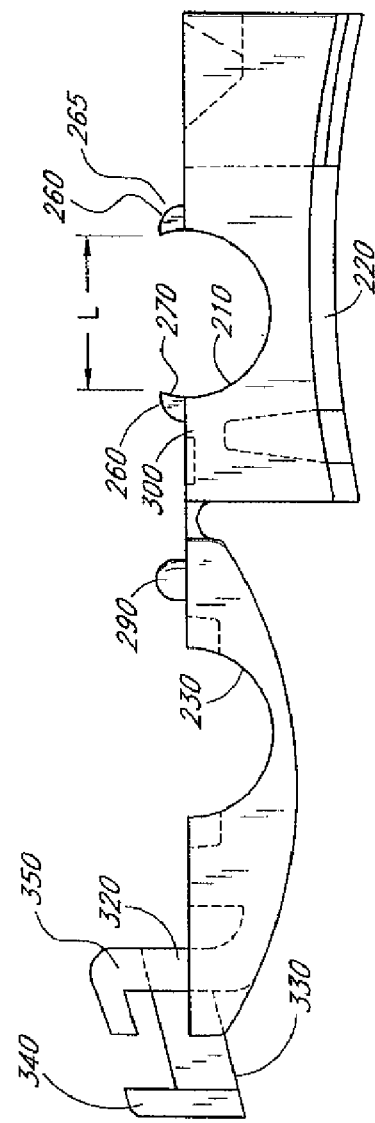
FIG. 4 illustrates a front view of the retainer of FIG. 2.

As seen in FIGS. 3 to 5, the lower side of the base 130 of the illustrated retainer 120 need not be perfectly flat, and may include contouring in order to assist in stabilizing the retainer 120 when placed on the skin of a patient. As can be seen in FIG. 4, the lower side 220 of the base may have a concave curved shape when viewed from the front along a longitudinal axis. The amount and radius of curvature may be varied depending on the expected location of usage or application of the securement device 100. Such a curved profile of the lower side 220 of the base allows for a closer match between the contour of the bottom of the base and the shape of the body of the patient. It will be appreciated that many common sites for insertion of medical lines which require securement will be located on anatomical regions exhibiting convex curvature, such as the arms, legs, shoulders, etc. By providing a concave bottom profile to the base 130 of the retainer 120, the retainer will rock less once placed upon the patient via the anchor pad 110. This will help prevent the retainer from pulling free from the anchor pad along the edges of the base 130, and also inhibits undesirable rotation of the retainer due to the bottom 220 of the base rolling along the body of the patient. For example, the curvature of the base 130 can be sized to generally match the curvature on a dorsal side of an average patient's hand for certain applications.

The bottom 220 of the base may also be angled in the longitudinal direction, as illustrated in FIG. 5. This angle is used in order to align the axis of the channel of the retainer with the desired incident angle with which the medical article is to contact the skin of the patient. A variety of different angles may be used, ranging from 0° to 45°, and more preferably from 5° to 25°. For instance, for the securement of arterial catheters, it is desirable for the angle of incidence of the catheter to the skin of the patient to be about 12.5°. For the securement of intravenous catheters, it is desirable for the angle of incident of the catheter to the skin of the patient to be about 7° to 15°. By angling the bottom 220 of the base 130 at the desired angle, which will depend upon the particular securement application (e.g., securing an arterial catheter, an intravenous catheter, etc.), the proper angle of incidence for a catheter can be maintained.

Figure 6:
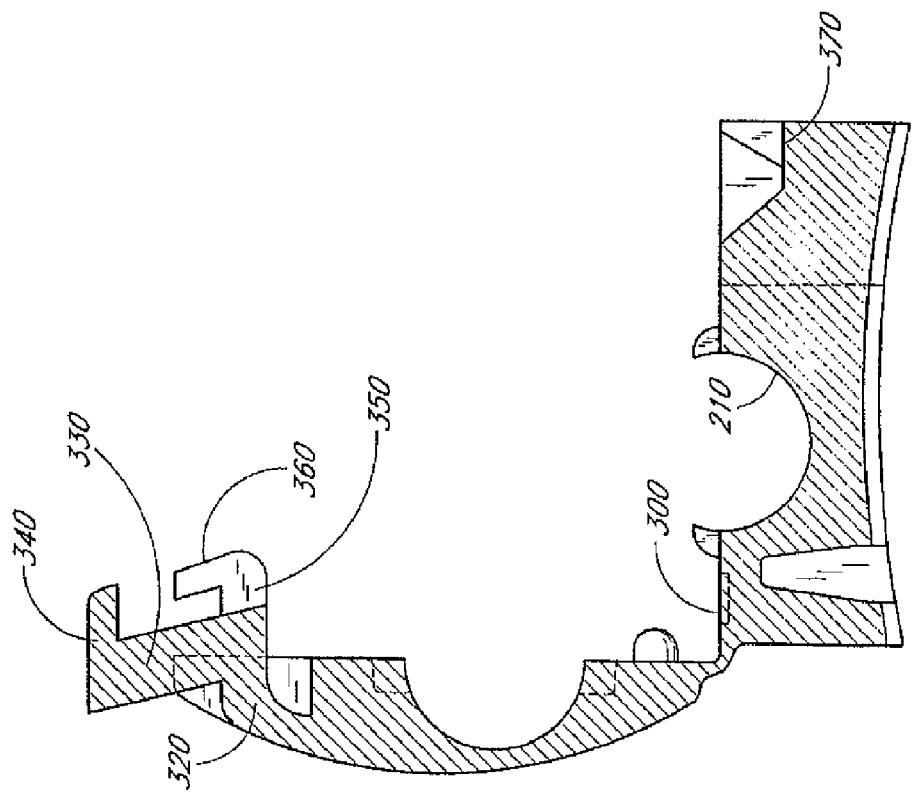
FIG. 6 illustrates a cross-sectional front view of the retainer of FIG. 3 taken through line 6-6.

The interior of the base 130 need not be completely solid. As shown in FIGS. 4 and 6, indentations and other empty regions or voids may be included on the bottom 220 of the base for a variety of reasons. For instance, certain indentations required by the manufacturing process may be located on the bottom 220 of the base in order to avoid exposing these indentations during use of the retainer. Those of skill in the art will recognize that these indentations need not be used, but may be included for reasons including but not limited to, lightening of the overall retainer structure, adding flexibility to the retainer, or providing a more advantageous surface for attachment between the base and the anchor pad.

It is advantageous for the longitudinal dimension of the base 130 to be sufficiently long to provide stability to the retained portion of the medical article along its length. In this way, the longitudinal length of the retained portion of the medical article is sufficient to inhibit the rocking of the medical article within the retainer 120. Also, the lateral dimension of the base 130 of the retainer desirably allows the healthcare provider to easily and naturally grip the base and also provides space on which to locate a hinge 200 and a portion of the latch 150.

In the shown embodiment, a longitudinal groove 210 is formed on the base 130, which extends from one longitudinal side of the base to the other. As illustrated in FIG. 2 and 4, this lower groove 210 has a generally semi-circular cross-sectional shape of constant radius. The size (i.e., radius) of the groove 210 may be chosen to match or approximate the size of various standard connector fittings, adaptors (e.g., catheter hubs) or other medical articles. By matching the size of the groove 210 to the external radius of the secured portion of a medical article, a more effective securement may be achieved. In addition or in the alternative, effective securement can also be achieved by the engagement of structures on the retainer and the medical article when the cover is closed. In other alternatives, securement may be achieved by the interaction of the shapes of the retainer and the secured medical article. Each of these approaches will be discussed in greater detail below.

The axis of the groove 210 in the illustrated retainer 120 lies parallel to the plane of the upper surface of the base 130. Although this configuration may be advantageous for securing particular medical articles, those of skill in the art will recognize that the axis of the groove 210 may be disposed at an angle relative to the upper surface of the base of the retainer for particular applications. For instance, the desired angle between the medical article and the patient could be created by angling the axis of the groove 210. In such cases, the bottom 220 of the base could remain roughly parallel to the surface of the patient's skin and the channel 250 formed by the groove could simply pass through the retainer at an angle relative to the patient.

The base 130 of the illustrated retainer 120 is attached to the upper surface 170 of the anchor pad 110, as is shown in FIG. 1. The base is desirably secured to the upper surface of the pad by a solvent bond adhesive, such as cyanoacrylate or other bonding material. One such adhesive is available commercially as Part No. 4693 from the Minnesota Mining and Manufacturing Company (now 3M).

As can be seen in FIGS. 2 to 4, the cover 140 of the illustrated retainer 120 has an elongate shape which desirably is substantially coextensive with the planar size and shape of the base 130 of the retainer 120. However, the cover need not be precisely the same size or shape as the base. For instance, the cover can be sized to extend beyond any of the lateral, transverse, or longitudinal edges of the base. The cover may also be sized so as to not extend to a particular lateral, transverse, or longitudinal edge of the base. The cover can also include a skirt or flange that extends over and/or about the base or any portion thereof. Such a flange or skirt may be advantageous in assisting in the handling of the retainer 120 by medical personnel, particularly while wearing gloves.

The cover 140 desirably has a sufficient size to cover the lower groove 210 in the base 130 and to accommodate a portion of the latch 150 and the hinge 200 which operate between the base 130 and the cover 140, as described below. The cover also desirably is of a dimension that provides for easy manipulation. For example, the cover's size easily accommodates the grasp of a medical attendant.

An upper groove 230 is formed on an inner side of the cover 140 corresponding generally in lateral position to the lower groove 210 formed in the base 130. In this way, when the cover of the retainer is moved over the base to establish the closed condition, the upper groove 230 and the lower groove 210 cooperate to form a channel 250 through the retainer 120 in a longitudinal direction. In the illustrated embodiment, the upper groove 230 generally has a semi-circular cross-sectional shape of the same radius as that of the lower groove 210; however, in some applications, the grooves 210, 230 can have differing radii of curvature.

The cover 140 is movably coupled to the base 130 by way of a flexible coupling or hinge 200. The hinge in the illustrated embodiment desirably comprises a flexible band that can take any number of forms to mechanically connect the cover to the base while permitting pivotal movement of the cover relative to the base so as to enable engagement or disengagement of these parts, as described below. It is this relative motion that is used to establish the open and closed conditions of the retainer. In the illustrated embodiment, the hinge is formed of flexible material, desirably of the same material from which the base and cover are comprised. Advantageously, the hinge is integrally molded with the base and the cover to form a unitary member, as noted above. The hinge is located at an outer edge of the base and the cover; however, the hinge need not be laterally located at an extreme end of the base or cover.

As best understood from FIG. 3, the width of the hinge 200 of the illustrated design, measured in the longitudinal direction, is desirably less than that of either the base 130 or the cover 140 to allow some leeway or play when engaging or disengaging the cover to the base. That is, this shape allows the hinge to twist to some degree to compensate for some manufacturing tolerances; however, the hinge can have at least as large of a longitudinal dimension as the base and the cover.

The hinge 200 is integrally formed along a common exterior surface of the cover and the base in the illustrated embodiment. The hinge generally has a U-shape when the cover is closed, and extends from both the base 130 and the cover 140 in the lateral direction to the side of the retainer. A gap, corresponding to a transverse height of the hinge 200, exists between the base and cover (see FIG. 7). This gap, however, can be reduced or eliminated from the retainer for some applications by using a different hinge design.

The hinge generally provides for relative motion between the first and second portion of the retainer. In the illustrated embodiment, the hinge 200 enables the cover 140 to move relative to the base 130 to establish an open condition and a closed condition for the retainer 120. In the open condition, as illustrated in FIGS. 2 to 4, the retainer is characterized by the exposure of the grooves 210, 230 in the base 130 and the cover 140 in the transverse direction. This is accomplished by spacing apart the base and the cover. In an open condition, the retainer 120 is capable of receiving a portion of a connector fitting or other medical article as described below. In a closed condition, as illustrated in FIG. 1, the retainer of the illustrated design is characterized by the cover 140 lying in contact or near contact with the base 130 so as to position the upper groove 230 above the lower groove 210. In this condition, the retainer 120 surrounds the received portion of the medical article and secures it within the channel 250 of the retainer.

The hinge 200 need not provide 180° of relative movement of the cover 140 and the base 130 to establish the closed and open conditions. For instance, the hinge can permit a smaller degree of movement (e.g., 90°) between the base and the cover while still providing enough space to transversely insert a portion of the medical article into the lower groove 210 of the retainer 120. Such a condition is still an open condition which can provide the necessary features discussed herein.

The grooves 210, 230 formed in the base 130 and the cover 140 of the retainer 120 define a channel 250 when the illustrated retainer is closed. As shown the channel 250 is capable of receiving a portion or length of the medical article and is generally configured to house, to preferably grip, and to secure this portion of the medical article. The channel can have a variety of configurations (e.g., tapered), as discussed above in connection with the grooves, in order to accommodate a particular medical article. For instance, the channel may have sides which are substantially straight and maintain a constant cross section along the longitudinal length of the channel. The channel may also be configured to have a tapered cross section such that the overall width of the channel is smaller at one longitudinal end than the other. The tapering may be at a constant rate along the length of the channel, or may occur only along certain portions of the length of the channel. The channel may also include either radial slots, providing regions of greater radius within the channel, or annular collars or reliefs, providing regions of smaller radius along the length of the channel. The channel may also taper along a curved profile, for instance, tapering to a smaller radius in the middle of the channel and then expanding again along the length of the channel.

These features may be used singly or in combination. In each case, the channel will be configured to receive and retain a portion of the medical article as described above. For instance, this can be accomplished by having the cross-sectional shape be substantially similar to at least a portion of the outer cross-sectional shape of the retained portion of the medical article. In addition, the size of the cross section of the channel will be chosen to fit within the overall transverse and lateral dimensions of the retainer. The operation of the channel to retain a medical article will be discussed further below.

In the illustrated embodiment, the channel generally has circular cross-sectional shape and a constant radius along its length. This can be seen in FIG. 8. Although the channel 250 can be formed in various shapes depending upon the desired application (i.e., depending upon a shape of the retained portion of the medical article for which the retainer is designed to be used), the channel 250 desirably has a sufficient length in the longitudinal direction to stabilize the connector fitting or other medical article, rather than act as a fulcrum for the fitting, as mentioned above. That is, the retainer 120 receives a sufficient length of the fitting to inhibit movement of the fitting in the lateral, longitudinal and transverse direction (i.e., to inhibit yaw, pitch and axial movement of the article).

Figure 11:
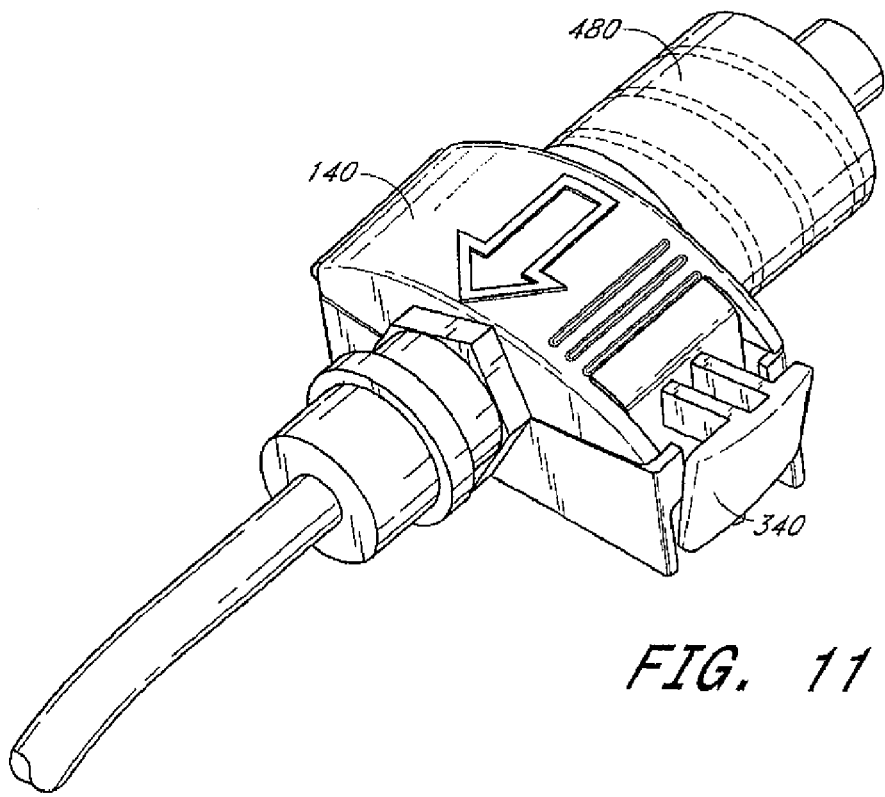
FIG. 11 illustrates a perspective view of the system of FIG. 10 with the retainer in a closed condition.

When the cover 140 establishes a closed condition for the retainer, a section of the medical article is captured within the retainer 120, as shown in FIG. 11. Thus, the retainer at least restricts, if not prevents, lateral and transverse movement of the retained section of the medical article.

As shown most clearly in FIGS. 2 and 4, the retainer 120 may optionally comprise one or more projections 260 which extend from the base 130 or cover 140 of the retainer in order to more firmly grip the retained portion of the medical article. In the illustrated embodiment, four such projections 260 are disposed upon the upper surface of the base 130 adjacent to the lower groove 210. Two projections are disposed on each lateral side of the groove 210. These projections 260 extend above the upper surface of the base 130 and may have a generally fin-shaped cross section, as seen in FIG. 4.

As shown in FIGS. 2-8, the projections 260 have a lateral outer face 165 disposed away from the groove 210, an inner surface 270 which forms a continuation of the surface of the groove 210, and two longitudinal faces which are generally vertical. Because the inner surface 270 of each projection 260 forms an extension of the surface of the lower groove 210, this groove is effectively extended beyond the upper surface of the base 130. As is most clearly illustrated in FIG. 4, the projections 260 can be used to effectively extend the lower groove 210 around the axis of the groove through an arc of greater than 180°, preferably about 200°.

By providing such optional projections 260 and their extensions to the lower groove 210, a snap-fit securement may be achieved between the lower groove 210 on the base 130 and the secured portion of the medical article, even while an open condition of the retainer is maintained. As will be discussed in greater detail below, if the diameter of the retained portion of the medical article is greater than the size of the lateral clearance L, shown in FIG. 4, between the opposing projections 260, then the medical article will be held within the lower groove 210 by the operation of the projections 260 and groove 210. In this way, the medical article may be placed in position prior to moving the cover 140 to establish the closed condition of the retainer 120 without concern that the medical article will shift while the medical practitioner is closing the cover of the retainer over the medical article.

A set of corresponding recesses 280 may be disposed upon the retainer 120 in order to provide a space for the projections 260 when the cover 140 is closed over the base 130. In the illustrated embodiment there are four such recesses 280 disposed upon the cover 140 of the retainer in positions which correspond to the locations occupied by the projections 260 when the cover is closed. Those of skill in the art will recognize that although the illustrated embodiment makes use of four projections disposed upon the base and three recesses disposed upon the cover, that other numbers of projections or locations for the projections may be used in alternate embodiments. For instance, two projections disposed to one side of the groove 210 may be used, with only a single projection to the opposite side of the groove. The projections may also be disposed upon the cover, and the corresponding recesses on the base. It is also possible to disposed projections on both the base and the cover, so long as appropriate recesses are placed at the complementary locations for each projection. These variations do not change the operation of the projections. In these ways, the projections may be used to surround the channel through an arc greater than 180° for the upper groove 230, as either an alternate or additional securement to the illustrated projections disposed around the lower groove 210.

In addition to the projections 260 and recesses 280 described above, one or more protrusion 290 and receptacle 300 pairs may also be disposed upon the first and second portions of the retainer. In the illustrated embodiment, the protrusions 290 are disposed upon the cover 140 of the retainer, and the receptacles 300 are disposed upon the base 130; however, the arrangement of the protrusions 290 and receptacles 300 on the cover and base can be reversed. As illustrated, each protrusion is disposed on the side of the cover nearer to the hinge 200 and the corresponding receptacles 300 are disposed upon the base in a position to receive at least a portion of the protrusion 290 when a closed condition is established. In the illustrated embodiment, a pair of protrusions and a corresponding pair of receptacles are used. However, any number of protrusions and receptacles may be used, and their disposition between the first and second portions of the retainer may be reversed or mixed as described above with regard to the projections and recesses.

When the cover 140 of the retainer is moved in order to latch the retainer in a closed condition, the protrusion 290 will move into the receptacle 300 on the base. This interengagement between the protrusion and the receptacle helps inhibit any twisting which may be imposed upon the cover relative to the base and also helps to align the latch components as will be discussed below.

In the illustrated embodiment, the receptacle 300 has a smaller transverse dimension than the transverse dimension of the protrusion 290. As a result, the protrusion prevents the cover 140 from moving into a position in which the cover lies completely flush upon the base 130. The protrusion provides a force which tends to push the cover away from the base. This force preferably is sufficiently large to assist the cover in popping open when the latch is released. This will be discussed in greater detail below.

Latch

In order to secure the first portion of the retainer relative to the second portion to establish a closed condition, some sort of latching mechanism can be provided to hold the first and second portions together. A variety of latching mechanisms are possible. The latching mechanism may be disposed partially on the base and partially on the cover, or entirely on one or the other component. It can be integrally formed with the retainer, or may be separate components which are formed separately and attached to the retainer. In the illustrated embodiment, the mechanism used to hold the cover 140 of the retainer in position above the base 130 for a closed condition (as shown in FIG. 1) is a latch 150 comprising interengaging structure disposed upon the cover 140 and base 130 of the retainer 120.

As shown in FIG. 2, the latch 150 is disposed primarily upon the cover 140 of the retainer, while appropriate receiver openings 310 into which a portion of the latch 150 are engaged are disposed upon the base 130 of the retainer. This particular geometry is formed integrally with the illustrated retainer 120. As seen most clearly in FIG. 2, the illustrated latch 150 comprises several components which are formed toward one lateral side of the cover 140. This latch 150 comprises an arm 320, an actuator bar 330, and a button 340.

As can be seen in FIG. 6, the arm 320 of the latch 150 is connected to the cover 140 of the retainer near the end of one lateral side of the retainer 120. This connection region is desirably somewhat flexible in order for the latch 150 to be movable relative to the cover 140. The arm 320 extends away from the connection to the cover, and is topped by a pair of tangs 350. Each tang 350 is disposed upon one longitudinal end of the arm 320 and extends transversely upward above the top of the arm (when the retainer has an open condition, as illustrated in FIGS. 2-5). Each tang 350 ends in a rounded hook 360 which includes a portion which curves laterally away from the channel 250 of the retainer. Desirably, the upper end of the tangs 350 are relatively blunt and smooth to prevent them from puncturing the gloves or skin of a healthcare provider or catching on other materials.

The actuator bar 330 is a lateral extension from the arm 320 which connects the arm 320 to the button 340. The button 340 may comprise a plate or other appropriate surface disposed roughly parallel to the arm 320 of the latch 150. The length of the actuator bar 330 allows the button 340 to be disposed at a lateral position which is beyond the lateral extent of the base 130 and cover 140 of the retainer when a closed condition is established. This may be advantageous in that the button 340 may be manipulated by a medical practitioner more easily if it protrudes beyond the lateral edge of the retainer 120, eliminating the need for precise positioning or pressure when releasing the latch 150, as will be described below.

Figure 7:
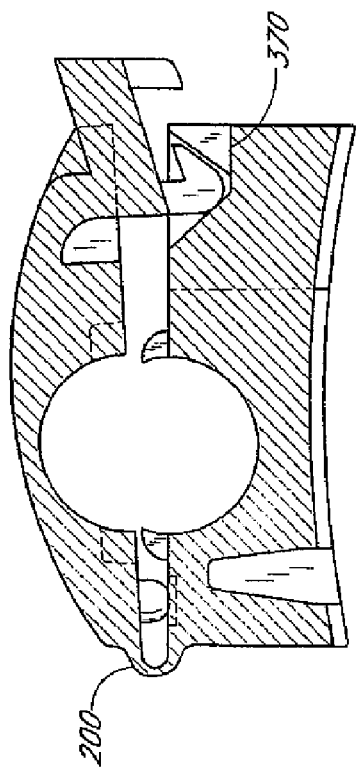
FIG. 7 illustrates a cross-sectional front view of the retainer of FIG. 6 as it approaches a closed condition.
Figure 8:
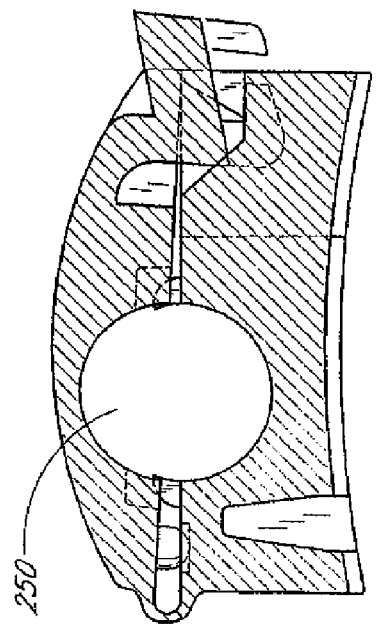
FIG. 8 illustrates a cross-sectional front view of the retainer of FIG. 6 in a closed condition.

When inward lateral pressure is exerted upon the button 340 of the latch 150 when the retainer is in a closed condition, the force is transferred from the button 340 to the actuator bar 330 and to the arm 320. The arm 320 will rotate about its connection to the cover 140, causing the entire latch 150 to flex inwardly toward the channel 250 of the retainer 120. As can be seen in FIGS. 6-8, as the latch 150 moves inwardly, the tangs 350 are deflected laterally toward the channel of the retainer.

In the illustrated latch, the button 340 is disposed with an angled outer surface such that this surface slopes inwardly from top to bottom (in a closed condition). Such positioning may be advantageous in minimizing unintentional disengagement of the latch 150 due to downward pressure from above upon the button 340.

In order to interoperate with the latch 150, appropriate receiver openings 310 for the tangs 350 are disposed upon the base 130 of the retainer. As seen in FIG. 2, the receiver openings 310 may comprise openings disposed upon the base 130. In the illustrated embodiment, these receiver openings 310 extend through the entire transverse thickness of the base 130, forming holes through the base. Those of skill in the art will recognize that the openings need not extend entirely through the cover in alternate embodiments making use of appropriately sized tangs.

The positioning of the receiver openings 310 upon the base is desirably such that they lie in a position beneath the tangs 350 of the latch when the cover 140 is moved over the base 130 in a closed condition (see FIG. 7). In the illustrated embodiment, the longitudinal position of the receiver openings 310 is also roughly the same as the longitudinal position of the recesses 280 corresponding to the projections 260, as described above. Such an arrangement may simplify manufacturing of the retainer, but it will be understood that such positioning is not required. However, it is desirable that the recesses 280 for the projections 260 correspond to the positioning of the projections and that the openings 310 for the tangs 350 correspond to the positioning of the tangs.

As seen most clearly in FIGS. 6-8 the receiver openings 310 may further comprise a shelf 370, disposed within the opening. The shelf 370 may be angled slightly so that the upper surface of the shelf (when the cover is in the closed position as in FIG. 8) angles upwardly as it extends toward the channel 250 of the retainer. The hook 360 of the tang 350 of the latch 150 will rest upon the shelf 370 of the receiver opening 310 in order to secure the cover 140 in position upon the base 130 of the retainer 120.

As can be seen in the cross-sectional views shown in FIGS. 6-8, the cover 140 may be pressed down onto the base 130 of the retainer in order to secure the cover in the closed position (illustrated in FIG. 8). When in the open position, as shown in FIG. 6, the retainer 120 is suitable for the insertion or removal of a portion of the medical article from the groove 210 of the base of the retainer. As the cover 140 is rotated about the hinge 200, it will eventually move into the position illustrated in FIG. 7.

As shown in FIG. 7, the protrusions 290 on the cover 140 of the retainer will move into the receptacles 300 on the base 130 of the retainer. As discussed above, the transverse depth of each receptacle 300 may desirably be less than the transverse extent of each protrusion 290. When the protrusion is fully within the receptacle, the protrusion becomes a fulcrum for rotation of the cover 140 relative to the base 130. Once this happens, the hinge 200 continues to flex, but the combination of the tension in the hinge 200 and the compression of the protrusion 290 into the receptacle 300 creates a force which tends to rotate the cover 140 of the retainer toward the open position.

Desirably, the upper surface of the shelf 370 may be angled such that when the cover 140 of the retainer is pressed down over the base 130, that the pressure from the underside of the shelf 370 upon the surface of the hooks 360 of the tangs 350 will cause the latch 150 to deflect inwardly toward the channel 250 of the retainer without the need for pressure upon the button 340. This is shown in FIG. 7.

As the cover 140 is pressed further down, the hook 360 of the tang 350 of the latch 150 will move below the shelf 370 of the receiver opening 310 on the base. At this point, the arm 320 will return toward its original more laterally disposed position, moving the hook 360 of the tang 350 over the shelf 370 of the opening 310. This configuration is illustrated in FIG. 8. Once in this position, the cover 140 is held down over the base 130 due to the contact between the shelf 370 and the hook 360, and the latch 150 is popped laterally outward, holding the hook 360 of the tang 350 in position upon the shelf 370.

In order to release the cover 140 from the closed position, a medical practitioner need only press laterally inward on the button 340 of the latch 150. This pressure, as discussed above, will result in the latch 150 deflecting toward the channel 250 of the retainer 120. As the latch 150 deflects inwardly, the hooks 360 of the tangs 350 of the latch are moved off of the shelf 370 of the receiver openings 310 in the cover (see FIG. 7).

Once the hooks 360 and shelf 370 are no longer engaged with one another, the compression of the protrusion 290 into the receptacle 300 on the base 130 will tend to push the cover 140 at least partially away from the base of the retainer. This allows for the retainer to be moved to an open condition without the need for a medical practitioner to pull up on the cover after the latch 150 is released from the receiver openings 310. This is the reverse of the process described above for closing the retainer.

The cover 140 may be secured into the closed position and released as often as necessary to allow for appropriate medical care. For instance, this allows for repeated attachment and reattachment of the medical article to the securement device 100. In addition, the hinge 200 connecting the cover 140 to the base 130 ensures that the cover will not be lost or misplaced in the process of attaching or detaching a medical article from the securement device. The medical practitioner wastes no time in searching for a cover, nor in orienting the cover prior to latching.

Connector Fitting

As discussed above, the connector fitting can be any portion of a medical article which is appropriate to attachment to a patient via the described securement devices. Most will include at least one elongated portion, and one or more regions of larger radius than the elongated portion. One exemplary medical article for use with the embodiment of the securement device described above will now be described with reference to FIGS. 9A and 9B. FIG. 9A illustrates a connector fitting 400 and an adaptor 410 for a catheter or similar medical device. The connector fitting 400 is preferably disposed upon the end of a medical line 420 which may be connected to a drip bag, blood monitor, or other fluid related medical apparatus.

The adaptor 410 includes a body that, in the illustrated embodiment, is configured as a catheter hub and tapers from a large radius to a smaller radius along its length. Although the illustrated adaptor has a generally constant taper so as to form a conical shape, those of skill in the art will recognize that the adaptor can have other shapes without altering the nature of the fundamental invention. For instance, the adaptor may have a body with a curved taper profile, or with a step-wise change in radius along the length of the adaptor body. The adaptor body can also include tabs or other protruding elements suitable for improving the grip of a medical practitioner on the adaptor.

The adaptor 410 also can include an external screw thread 430 on the outside of the conical body near the end with the larger radius. The screw thread 430 can be used in association with a spin nut (described below) of the connector fitting in order to securely interconnect the connector fitting and the adaptor.

The connector fitting 400 comprises an elongated body 440 which is attached to the end of a medical line 420. The connector fitting 400 also comprises a portion which is desirably tapered along at least part of its longitudinal length so as to allow the end of this region to fit within the tapered conical portion of the adaptor 410. The tapered portion 450 of the connector fitting 400 also preferably includes a centrally disposed lumen which communicates with the lumen of the medical line. When the connector fitting 400 is inserted into the adaptor 410, the lumen of the connector fitting is disposed in fluid communication with the lumen of the adaptor. This provides fluid communication between the medical line 420 and the patient.

As seen in FIG. 9A, the connector fitting 400 can also have at least one radially extending member 460 disposed upon an end of the elongated body 440 of the fitting opposite the tapered end 450. As shown in the FIGURE, it may be advantageous for the radially extending member 460 to extend completely around the circumference of the connector fitting 400. A second radially extending member 470 may also be disposed upon the elongated body 400, as may additional radial members (not shown). Those of skill in the art will recognize that the radially extending member or members need not have any particular shape or longitudinal thickness. Additionally, the radially extending members need not have the same shape. For instance, the first radially extending member 460 can have the hexagonal shape illustrated and the second radially extending member 470 can have a circular shape.

A spin nut 480 is disposed upon the connector fitting 400 around the elongated body 440 of the fitting. The spin nut 480 is substantially cylindrical in form and is able to move upon the connector fitting 400. The spin nut 480 is capable of both rotational motion around the axis of the connector fitting and axial motion in both the proximal and distal directions along the length of the elongated body 440 of the fitting. The spin nut 480 also includes internal screw threads 490 which are illustrated with phantom lines in FIG. 9A.

Figure 9B:
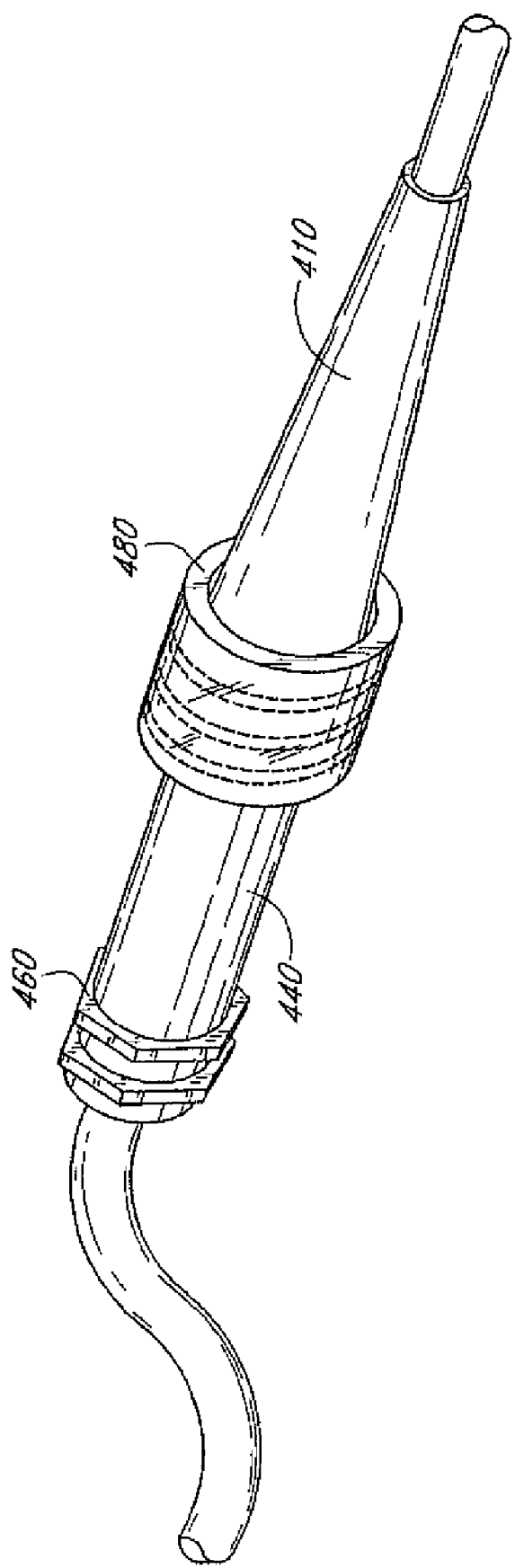
FIG. 9B illustrates a perspective view of the connector fitting of FIG. 9A with the spin nut secured in the forward position and secured to a catheter adaptor.

As shown in FIG. 9B, when the tapered end 450 of the connector fitting is inserted into the wide end of the adaptor 410, the spin nut 480 may be moved toward the tapered end 450 of the connector fitting 400 and twisted so as to engage the screw thread 490 of the spin nut with the screw thread 430 of the adaptor 410 and lock the connector fitting 400 to the adaptor 410. Note that because the securement device 100 described above will be used to attach to the elongated tubular portion 440 of the connector fitting 400, there is no need to use a connector fitting which includes wings or suture holes.

Additional details not necessary to repeat here are disclosed in assignee's co-pending application entitled MEDICAL DEVICE CONNECTOR FITTING, application Ser. No. 09/767,207, filed on Jan. 22, 2001, the entirety of which is hereby incorporated herein by reference.

Operation

Figure 10:
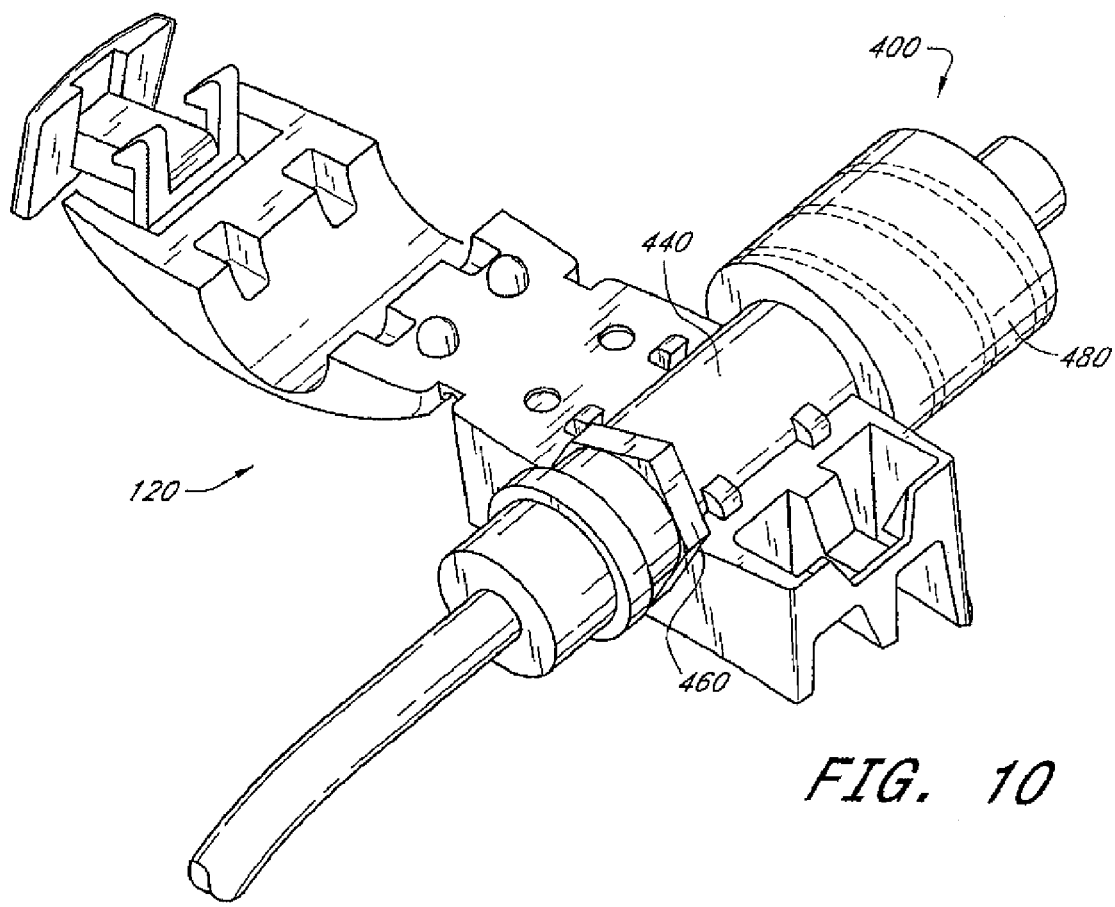
FIG. 10 illustrates a perspective view of the connector fitting of FIG. 9B in position upon the retainer of FIG. 2.

As illustrated in FIGS. 10 and 11, medical personnel can secure a connector fitting 400 (or other medical article) to a patient using the above-described securement device 100 or a readily apparent modification thereof. The medical practitioner first opens the retainer 120 to expose the lower groove 210 on the base 130. When the retainer 120 is in the open condition, the connector fitting 400 or other medical article can be aligned over the groove 210. The connector fitting 400 can then be pressed into the groove on the base. If the connector fitting 400 has a diameter greater than L (shown in FIG. 4) and less than the diameter of the groove 210, the projections 260 will create a snap-fit between the connector fitting 400 and the base 130. This configuration is shown in FIG. 10.

Note that prior to the engagement of the connector fitting 400 to the retainer 120, it may be desirable for a medical practitioner to confirm that the spin nut 480 of the connector fitting is moved in the longitudinal direction toward the catheter adaptor 410, as shown in FIG. 9B. In this position, the elongated tubular body 440 of the connector fitting 400 which is located between the spin nut 480 and the radially extending member 460 is available for insertion into the groove 210 of the base of the retainer.

Furthermore, because the spin nut 480 and radially extending members 460, 470 have a greater radius than the tubular body 440 of the connector fitting and the lower groove 210, the spin nut and radial member will not slide into or through the groove of the base. In this way, the spin nut 480 and radial member 460 form extensions which inhibit the longitudinal migration of the connector fitting 400 in either direction through the channel 250 of the retainer.

Once the connector fitting 400 or other medical article is in position upon the base 130 of the retainer, the cover 140 may be moved over the base of the retainer and latched into a closed condition as described above and shown in FIG. 11. In this position, the openings 310 on the base 130 are engaged with the tangs 350 of the latch 150 on the cover 140. Once in this closed condition, the retainer 120 surrounds the elongated body 440 of the connector fitting 400 or other medical article lying within the channel 250. This inhibits any transverse or lateral motion of the medical article relative to the retainer. Longitudinal motion of the medical article is inhibited by the portions of the medical article which are of larger radius than the channel as described above. Specifically, in the illustrated embodiment, the radially extending member 460 and the spin nut 480 are desirably unable to pass through the channel of the retainer.

In order to minimize the degree of longitudinal movement of the catheter fitting 400, the longitudinal length of the channel 250 of the illustrated retainer generally matches the received length of the catheter fitting 400 that extends between the spin nut 480 and the radially extending member 460 with the spin nut 480 fully threaded onto the catheter adaptor 410. Some play, however, is desirably provided in order to permit the catheter fitting 400 to be inserted into the retainer even if the spin nut is not fully threaded onto the catheter adaptor 410.

The retainer 120, being attached to the anchor pad as described above, may be positioned and secured on the patient near the securement site for the medical article either before or after the placement of the medical article into the retainer. In many cases it will be desirable for the medical practitioner to attach the anchor pad 110 and retainer 120 to the patient prior to securing the medical article. It should also be noted that because the retainer 120 may have an angled bottom 220, the lower side of the securement device 100 should be located toward the insertion site on the patient in order to properly angle the channel toward the skin of the patient and not away from the skin of the patient.

The medical practitioner may first remove one portion of the release liner 180 from the anchor pad 110 by gripping the pull tab 190 and pulling the liner 180 away from the lower surface 160 of the anchor pad 110. This exposes the adhesive layer of the anchor pad, which may then be applied to the skin of the patient near the site where the medical practitioner desires to secure the connector fitting 400 or other medical article. The remainder of the release liner 180 may then be removed and the securement device 100 fully attached to the skin of the patient. At this time, the cover 140 of the retainer may be opened and the connector fitting 400 secured to the retainer 120 as described above.

To release the medical article from the retainer, the medical practitioner presses laterally upon the button 340 of the latch 150, releasing the tangs 350 from the openings 310 of the base 130, and causing the cover to pop slightly open. The cover may then be fully opened and the medical article removed from the lower groove 210 on the base of the retainer, if desired. Medical articles may be inserted and removed from the same securement device repeatedly using the described system.

For example, if a particular catheter is being changed, the first catheter may be released from the securement device, and then the second catheter secured to the same device without ever removing the retainer and anchor pad from the skin of the patient. Similarly, if the same catheter is to be used, but a different medical line is to be connected, the medical practitioner may release the first connector fitting from the retainer, separate the connector fitting from the catheter adaptor, and then connect the connector fitting belonging to the new medical line to the same catheter adaptor. This new catheter adaptor may now be secured to the retainer as described above.

Another usage of the described embodiments may involve keeping the same medical line, but changing the securement device. This may be advantageous in order to move the site at which the adhesive of the anchor pad is attached to the skin of the patient or to clean the area near the securement site. In these cases, the medical line may be removed from a first securement device attached to a patient, the first securement device removed from the patient, any necessary cleaning or treatment of the skin performed, a second securement device positioned upon the patient, and then the medical line secured to the second securement device.

Slotted Retainer

An additional embodiment of a medical line securement device having a retainer including slots along the length of the channel will now be described with reference to FIGS. 12-14. Except as otherwise noted, the above description of the retainer, the connector fitting, and the operation of the retainer upon the connector fitting or other medical article will apply. Throughout this description, the use of a reference number also used in the above description will indicate an element substantially as already described above.

Figure 12:
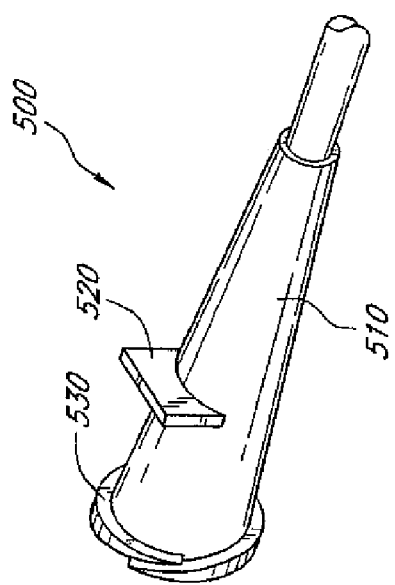
FIG. 12 illustrates a perspective view of a catheter adaptor having a radially projecting tab.
Figure 13:
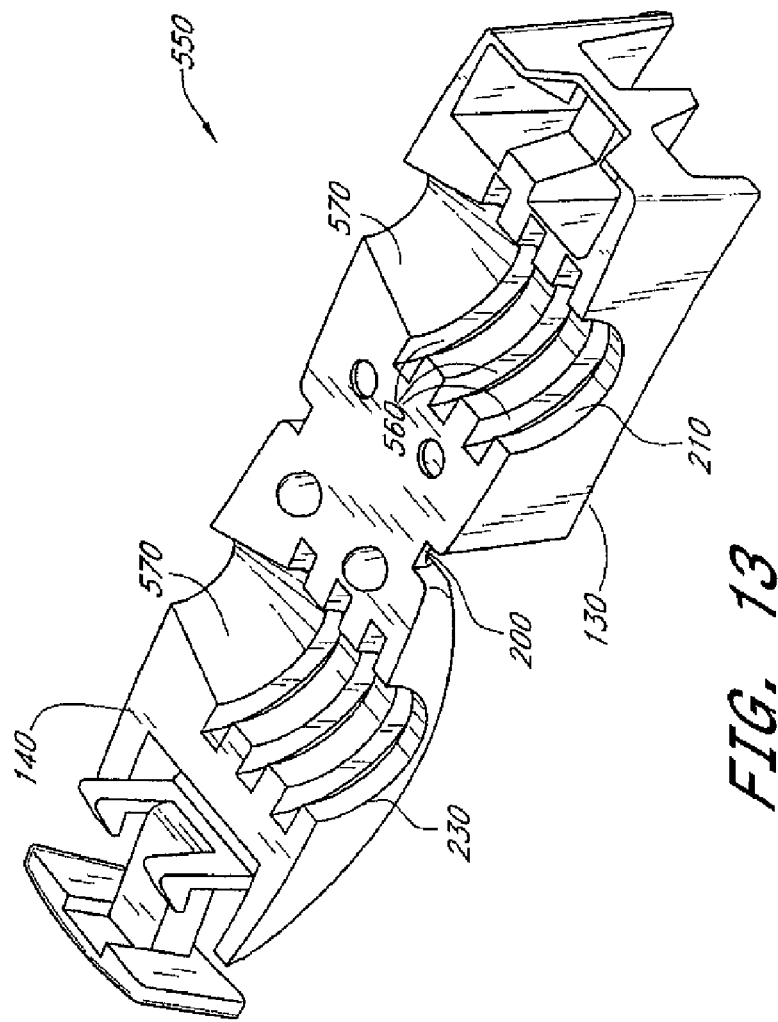
FIG. 13 illustrates a perspective view of a retainer of another embodiment of a medical line securement device in accordance with the disclosure herein.
Figure 14:
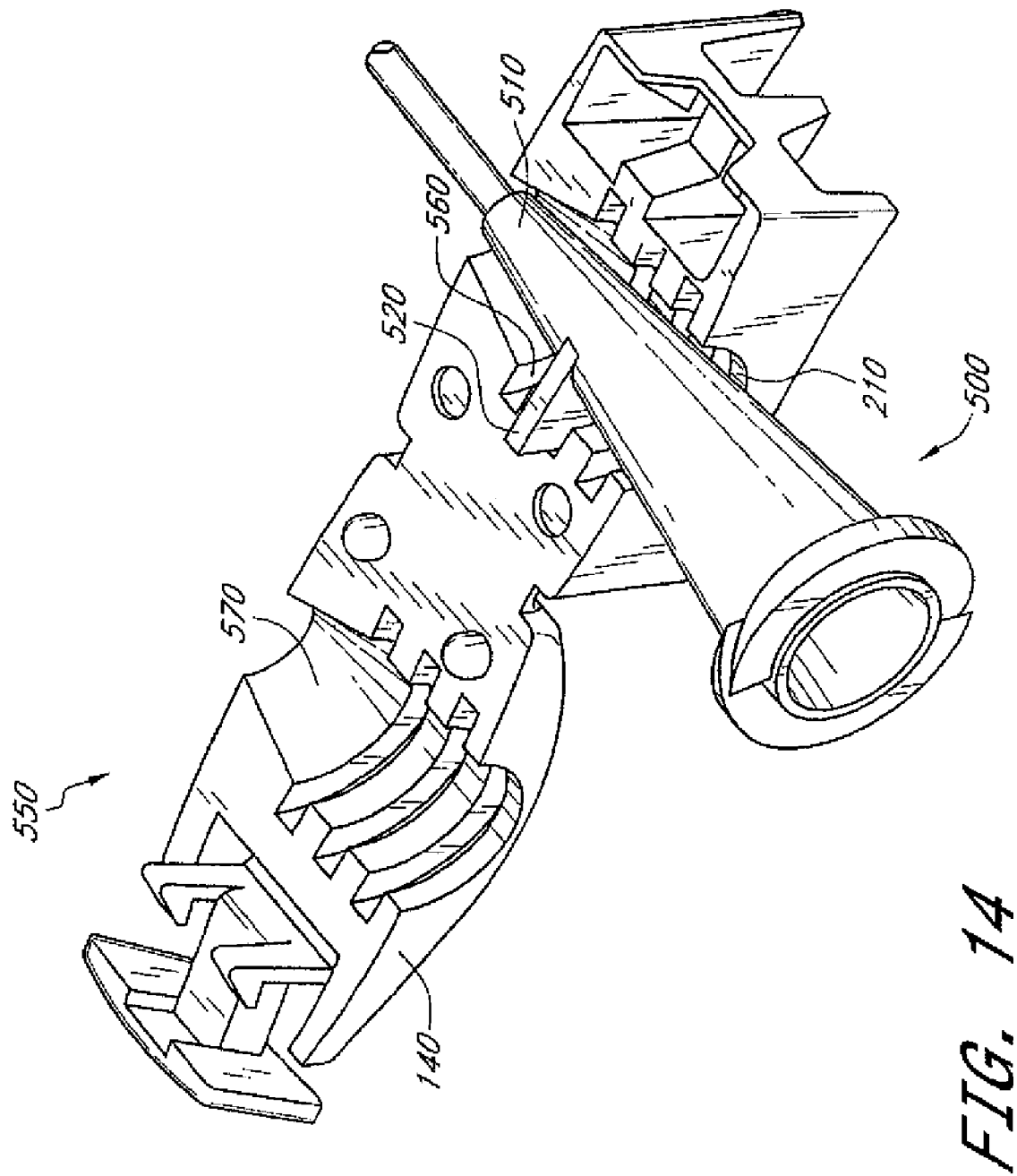
FIG. 14 illustrates a perspective view of the catheter adaptor of FIG. 12 in position upon the retainer of FIG. 13.

As illustrated in FIGS. 12-14, the alternate retainer shown can include slots in addition to the features described above.

This may be advantageous when securing medical articles which include radially extending regions which are not separated sufficiently to allow entire channel of the retainer to grip the medical article between the radially extending regions. In addition, such a retainer may be used to secure medical articles in which there is only a single radially extending region.

One example of a medical article suitable for securement using this embodiment of the retainer is shown in FIG. 12. This medical article is a catheter hub 500, which is formed from a tapering body section 510. In general configuration, such a catheter hub 500 may be similar to the catheter hub 410 shown in FIG. 9A and described above. However, as can be seen in FIG. 12, an additional radially projecting element, such as a lateral tab 520 is disposed at a position along the length of the body 510 of the hub. This tab 520 can allow a medical practitioner to more easily apply longitudinal pressure to the catheter adaptor while working with it.

In the illustrated system, the tab 520, also sometimes known as a 'push pad' or 'push tab', has substantially the same lateral width as the portion of the catheter adaptor 500 from which it extends. If desired, the tab 520 can be configured to be wider than the body 510 of the adaptor in order to provide a larger push surface. It will also be understood that it may be desirable to place a plurality of such radially projecting elements upon the a catheter hub for a variety of reasons. Such additional tabs may extend in different directions, or may be placed at different longitudinal positions along the length of the catheter adaptor.

Although the radially projecting element illustrated in FIG. 12 is a tab, it will be understood by those of skill in the art that the projecting element may take alternate forms as well. For instance, the radial projecting element may comprise an annular ring or collar that extends around the body section 510 of the adaptor 500.

The catheter adaptor 500 of FIG. 12 may also desirably include an external screw thread 530, as described above with respect to the catheter adaptor of FIGS. 9A and 9B. This screw thread 530 allows the adaptor 500 to be joined to a connector fitting or other medical article via a spin nut in substantially the same manner as described above.

FIG. 13 illustrates a retainer 550 for use with a catheter adaptor 500 as described above. Although certain features of the retainer 550 are specifically configured for use with an adaptor 500 as illustrated in FIG. 12, it will be understood by those of skill in the art that such a retainer may be used with other adaptors or medical lines as well.

As shown in FIG. 13, the general structure of the retainer 550 is similar to that of the retainer 120 as described above with reference to FIGS. 2-8. The retainer 550 comprises a base 130, cover 140, latch 150, hinge 200, and lower and upper grooves 210, 230. These are substantially as described above.

In addition, the retainer 550 of FIG. 13 also includes one or more slots 560 which may be disposed upon the lower or upper grooves 210, 230. These slots 560 may extend circumferentially about the axis of the channel 250 formed by the grooves 210, 230 when the cover of the retainer 550 is in the closed position. Each slot has a longitudinal length sufficient to accept a radially projecting element of the retained medical article. In particular, it may be desirable for the longitudinal length of each slot to be sufficient to receive the tab 520 of a catheter adaptor 500 as described above. Each slot 560 also desirably has a radial extent sufficient for the tab 520 of the adaptor 500 to be received regardless of the rotation of the adaptor about its axis. In other words, the slot 560 may receive the tab 520 whether the tab is pointing up, down, to either side, or at any other angle about the axis of the adaptor.

As shown in FIG. 13, these slots 560 may be substantially annular in form. However, those of skill in the art will recognize that each slot need not have identical radial extent, and that the radial extent of each slot need not be uniform about the axis of the channel 250. In addition, each slot need not circumscribe the channel 250 entirely. For instance, slots may be disposed upon the base 130 of the retainer 550, but not upon the cover 140. Such an arrangement will not support capturing the tab 520 of the adaptor 500 in as many radial positions, but may be desirable for certain applications.

In the illustrated design, three annular slots 560 are disposed upon the lower and upper grooves 210, 230. In order for each slot 560 to properly receive a radially projecting element from the retained portion of the medical article, the longitudinal extent of each slot 560 may preferably be about 0.005 of an inch larger than the projecting element. Such an arrangement may be desirable to minimize longitudinal movement of the retained portion (e.g., the tab 520), of the medical article.

FIG. 14 illustrates a catheter adaptor 500 placed within the retainer 550. As can be seen, the tab 520 of the adaptor 500 lies within one of the slots 560 of the retainer 550. In addition, the body 510 of the adaptor 500 generally lies within the lower groove 210 of the retainer. When the cover 140 of the retainer 550 is moved over the base 130 such that the retainer is in the closed condition, the body 510 of the adaptor 500 will lie within the channel 250 of the retainer 550, and the longitudinal walls of the slot 560 will inhibit axial migration of the adaptor 500 through the channel 250 of the retainer 550.

In addition, if used with a connector fitting 400 in which a portion of the connector fitting, such as the spin nut 480, has a greater radial size than the size of the channel 250 of the retainer 550, the spin nut 480 will inhibit axial motion in one direction through the channel 250 of the retainer as well.

The edges of each slot 560 may also desirably be chamfered so as to ease the insertion of a radially projecting element into any slot 560. By having the edges of each slot chamfered, it becomes possible to move a projecting element into a slot even if the initial alignment between the center of the slot and the center of the projecting element is not perfect. The use of chamfered edges on the slots 560, as well as the presence of slots located at multiple longitudinal positions along the length of the channel 250 allow for a medical article to be placed over the lower groove 210 of the retainer 550 with only coarse alignment with the axis of the groove 210 and then to move into an appropriate slot 560 within the retainer as the medical article is pressed down into the retainer 550 from above.

These features help make the use of the retainer less technique sensitive and thereby allow the healthcare provider to more easily insert the medical article into the retainer quickly and effectively. These multiple slot positions can also provide different insertion locations to accommodate the various ways a connector fitting and a catheter adaptor may be joined.

For example, in some applications such as with intravenous catheterization of neonates, a healthcare provider may not engage the spin nut 480 with the adaptor 500. As such, the distance between the radially extending tab 520 and the spin nut 480 will differ from when the spin nut 480 is threaded onto the catheter adaptor 500 fully. Another possible benefit of multiple slots 560 being disposed along the channel is that this can allow the retainer to receive medical articles which include a plurality of radially projecting elements. For example, if the catheter adaptor 500 or connector fitting 400 has a plurality of annular rings, this portion of the medical line may be secured by an appropriately sized retainer 550 in accordance with the embodiments illustrated herein.

As shown in FIG. 13, the lower and upper grooves 210, 230 of the retainer 550 may also include a tapered region 570. As discussed above, such a tapered region may provide a more secure fit between a medical article having a similar shape and the retainer 550. In addition, this tapered region 570 may prevent migration of a tapering medical article through the retainer in at least one direction because the larger portions of the medical article are inhibited from moving through the smaller opening at the tapered end of the channel 250. It will be understood that the use of slots upon a retainer does not require the use of a tapered region.

Retainer with Compressible Member

Figure 15:
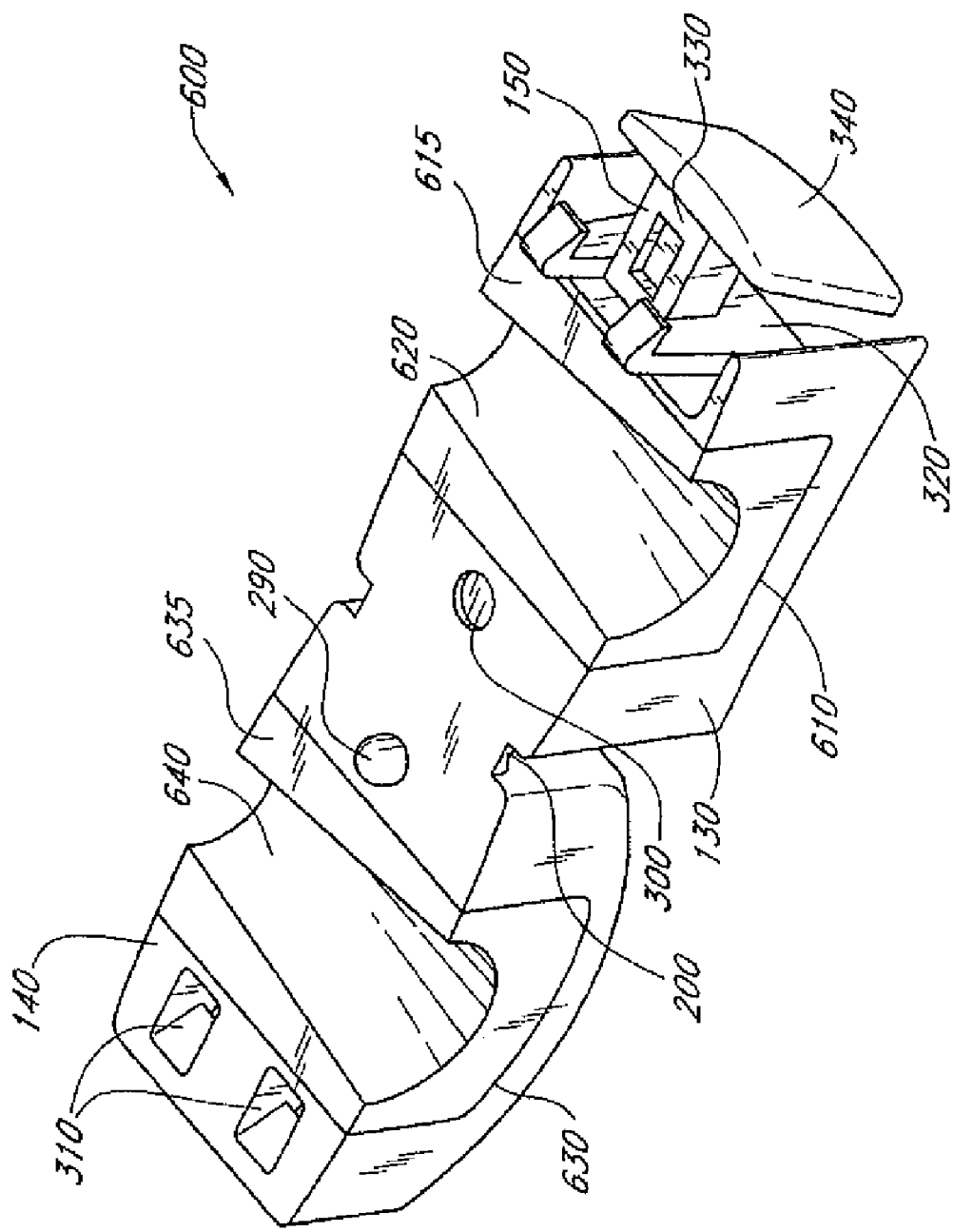
FIG. 15 illustrates a perspective view of a retainer of yet another embodiment of a medical line securement device in accordance with the disclosure herein.
Figure 16:
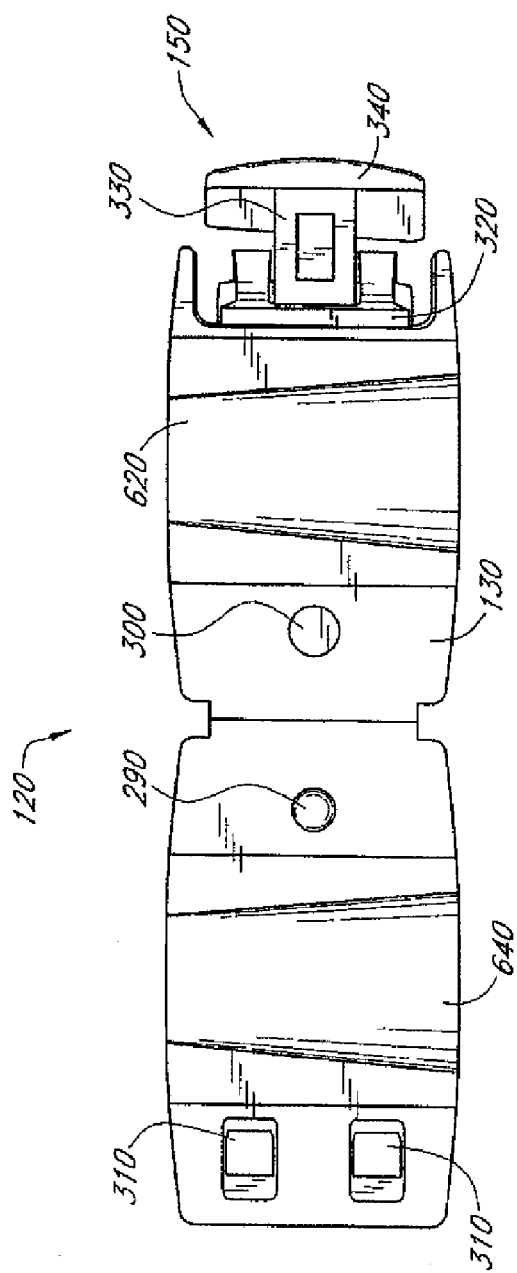
FIG. 16 illustrates a top view of the retainer of FIG. 15.
Figure 17:
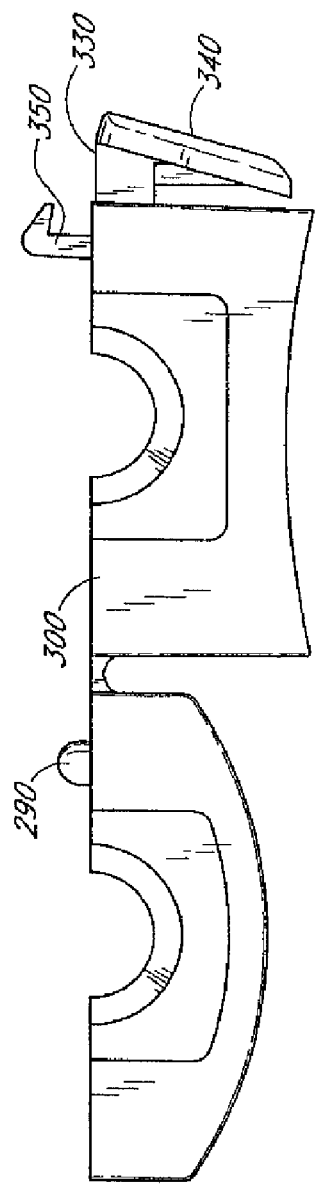
FIG. 17 illustrates a front view of the retainer of FIG. 15.

Another design for a medical line securement device is illustrated in FIGS. 15-17 and described herein. This retainer is as is described above with respect to the retainer of FIGS. 2-8, with the exception of having a tapered channel cross-section made of a compressible material, and having the latch positioned on the base instead of the cover of the retainer. Except as otherwise noted, the above description of the retainer, the connector fitting, and the operation of the retainer upon the connector fitting or other medical article will apply.

In the retainer shown in FIG. 15, the retainer 600 is still substantially comprised of a base 130 and a cover 140. However, the base 130 does not have a groove. Instead, the base includes a lower housing 610. The lower housing 610 may take any geometric form such as a trough or channel which passes through the longitudinal thickness of the base 130. In the illustrated retainer 600, the lower housing 610 has a generally three sided shape. The lower housing 610 comprises three surfaces where two opposing surfaces are parallel to each other and generally perpendicular to the third surface. A lower compressible member 615 is disposed in the lower housing 610. The lower compressible member 615 fills the lower housing 610, and includes a lower compressible groove 620. This compressible groove is substantially as the lower groove 210 described above with respect to FIGS. 2-8, except that it is constructed of a compressible material, as described more fully below.

The cover 140 of the illustrated retainer 600 includes an upper housing 630. Similarly to the lower housing 610, the upper housing 630 generally replaces the groove 230 of the system shown in FIGS. 2-8. The upper housing 630 includes an upper compressible member 635. Both of the housings are sized such that the space within the upper housing 630 and lower housing 610 is sufficient to accommodate various sizes of catheters or other medical articles when the retainer 600 is in a closed condition. The upper compressible member 635 includes an upper compressible groove 640.

The upper compressible groove 640 and the lower compressible groove 610 of the shown retainer 600 may have any of the properties described above with respect to the upper and lower grooves 230, 210 of the basic retainer 120. For instance, the illustrated upper and lower grooves have a tapered cross section. The upper compressible groove 640 and the lower compressible member 620 together form a compressible channel when the retainer 600 is in a closed condition.

The lower and upper compressible members 615, 635 of the retainer 600 are comprised of a material that is compressible and compliant that conforms to various shapes. This material can be more compressible than the material of the base 130 and cover 140. Preferably, the compressible members 615, 635 are sufficiently pliant that they may deform so as to accommodate the any protruding geometry of a retained medical article, such as the tab 520 of the catheter adaptor shown in FIG. 12. Many suitable materials are capable of large deformations to surround a medical article and provide a secure fit. Suitable pliant materials include, for example, but without limitation: plastics, polymers, elastomers, foams, polyester, thermoplastics, silicon elastomers, urethane epoxies, thermoplastic elastomers, and thermoset plastics and the like. In particular, Kraton polymer compounds, such as Dynaflex G2706 available from GLS Corporation is used in the illustrated embodiment.

The compressible grooves 620, 640 in the pliant material of the compressible members 615, 635 are preferably sized so that the channel formed by the compressible grooves is somewhat smaller than the portion of the catheter adaptor to be retained. Thus, when the retainer is in a closed condition, the pliant material will be compressed to provide a force against the adaptor or other retained medical article. This force inhibits longitudinal displacement of the adaptor.

In addition or as an alternative, the pliant material may be pressed into an appropriate recess or groove disposed upon the adaptor or other retainer medical article. By expanding into such a recess, the pliant material can provide an additional gripping force to retain the adaptor. For instance, it may be desirable to place a pliant, compressible material into an annular slot disposed upon the retainer and to allow the pliant material to extend toward the axis of the channel above the surface of the remainder (non-pliant) of the channel. Such an arrangement can be used to create a compressible collar that can be useful for providing a frictional engagement of a secured medical article.

Additionally, the surface of the compressible grooves 620, 640 may include an adhesive or a surface treatment to further increase the frictional force between the secured section of medical article catheter adaptor and the retainer 600. Suitable surface treatments include those which increase the "grip" provide by the channel walls, for example by creating a high friction surface within the channel. Examples of such treatments include, without limitation, corona treating, chemical treating, scoring, and adhesive treating. Suitable adhesive treatments are those which provide for releasable traction, rather than permanent bonding, between the channel and the medical article.

Suitable adhesive treatments for the surface of the compressible grooves include hot-melt adhesives which retain a soft tacky surface at room temperature. Those skilled in the art will recognize that the adhesives other than hot-melt adhesives may serve a similar function. The adhesive may be disposed upon the grooves 620, 640 by various means, including being applied to the surfaces by spraying the adhesive into the grooves. Those of skill in the art will recognize that there are many other surface treatments or adhesives that can be used to increase the friction between the retainer and the catheter adaptor. Additionally, both the upper and lower grooves need not be treated in the same way.

The operation of the compressible grooves upon the body of a medical article, such as a catheter adaptor is generally as described above. In addition, because the channel formed by the compressible grooves in a closed condition of the retainer may be of a smaller radius than at least a portion of the retained medical article, the compressible members will deform and apply a pressure to the body of the retained medical article. This pressure increases the normal force acting upon the medical article thereby increasing the frictional force between the medical article and the retainer 600. This pressure helps to inhibit any transverse or lateral motion of the medical article relative to the retainer 600. This pressure also inhibits linear movement or rotation of the medical article about the longitudinal axis of the channel.

As can be seen in FIGS. 15-17, a single protrusion 290/receptacle 300 pair is disposed upon the base and cover of the retainer 600. Although only a single pair is disposed, the operation of the protrusion and receptacle are substantially as described above with respect to the retainer 120 of FIGS. 2-8.

It may also be noted that the latching mechanism of the retainer 600 is disposed upon the base 130 of the retainer 600, rather than upon the cover 140. Although the latch 150 is disposed on the base 130, and the receiver openings 310 are disposed upon the cover, the components and operation of the latch 150 is substantially as described above.

Because two different materials may be used for the construction of the base 130 and cover 140 of the retainer and the compressible members 615, 635, manufacturing may require an additional step when compared to the retainer 120 of FIGS. 2-8. For instance, both the compressible members and the base and cover may be formed by injection molding. In a preferred mode of manufacturing, the entire retainer 600 is integrally formed by a two-stage, over-molding injection process. The base 130, cover 140, latch 150 and hinge 200 can be formed in the first stage from a first material. The upper compressible member 635 and lower compressible member 615 can be formed in an additional stage from a second material. By using this method, the entire retainer can be formed unitarily and without involving the extra step of mechanically joining separately manufactured parts. However, alternatively, an adhesive or ultrasonic welding can be used to attach a pre-molded upper compressible member 635 and lower compressible member 615 to the upper and lower housings 630, 610. It will be recognized that other materials or manufacturing processes as known in the art may also be used.

Additional Variations

Other embodiments of the medical line anchoring system described herein are briefly described below. Each of these variations may present a features which differs from the retainers described above. However, except as noted, the operation of these variations is substantially as described with respect to the foregoing retainers.

In one variation, the channel of the retainer may be configured to both a portion of a connector fitting, and a portion of a catheter adaptor. This can be particularly effective when used with compressible members. The pliant material of the retainer can deform to the shape of both the connector fitting and the catheter adaptor and inhibit adaptor movement. Gripping the combination of the connector fitting and catheter adaptor in the region where they are joined to one another may be advantageous when a tapered catheter adaptor has neither a projecting element nor a rough surface. This embodiment may be capable of gripping a catheter assembly, such as the joined connector fitting and catheter adaptor, even when significant forces are applied to the catheter assembly in the longitudinal direction toward the connector fitting and away from the catheter adaptor.

Another usage of the systems and devices described herein is to provide a medical line kit which includes a retainer and anchor pad already disposed upon an appropriate connector fitting or other medical article. Such an arrangement can allow for more streamlined placement of a medical line onto a patient. After inserting the catheter with its adaptor into the patient, the connector fitting can be inserted into the lumen of the catheter adaptor and then secured in position, e.g., via the spin nut of the connector fitting. This can be done with the securement device already in position upon the connector fitting. Because the retainer is already placed upon the connector fitting 400, the medical practitioner can simply remove the liner 180 from the anchor pad 110 and place the lower surface 160 of the anchor pad onto the patient at the appropriate location.

The various embodiments of securement devices and techniques described above thus provide a number of ways to provide safe and releasable securement for medical articles to the skin of a patient. In addition, the techniques described may be broadly applied for use with a variety of medical lines and medical procedures.

Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Figure 18:
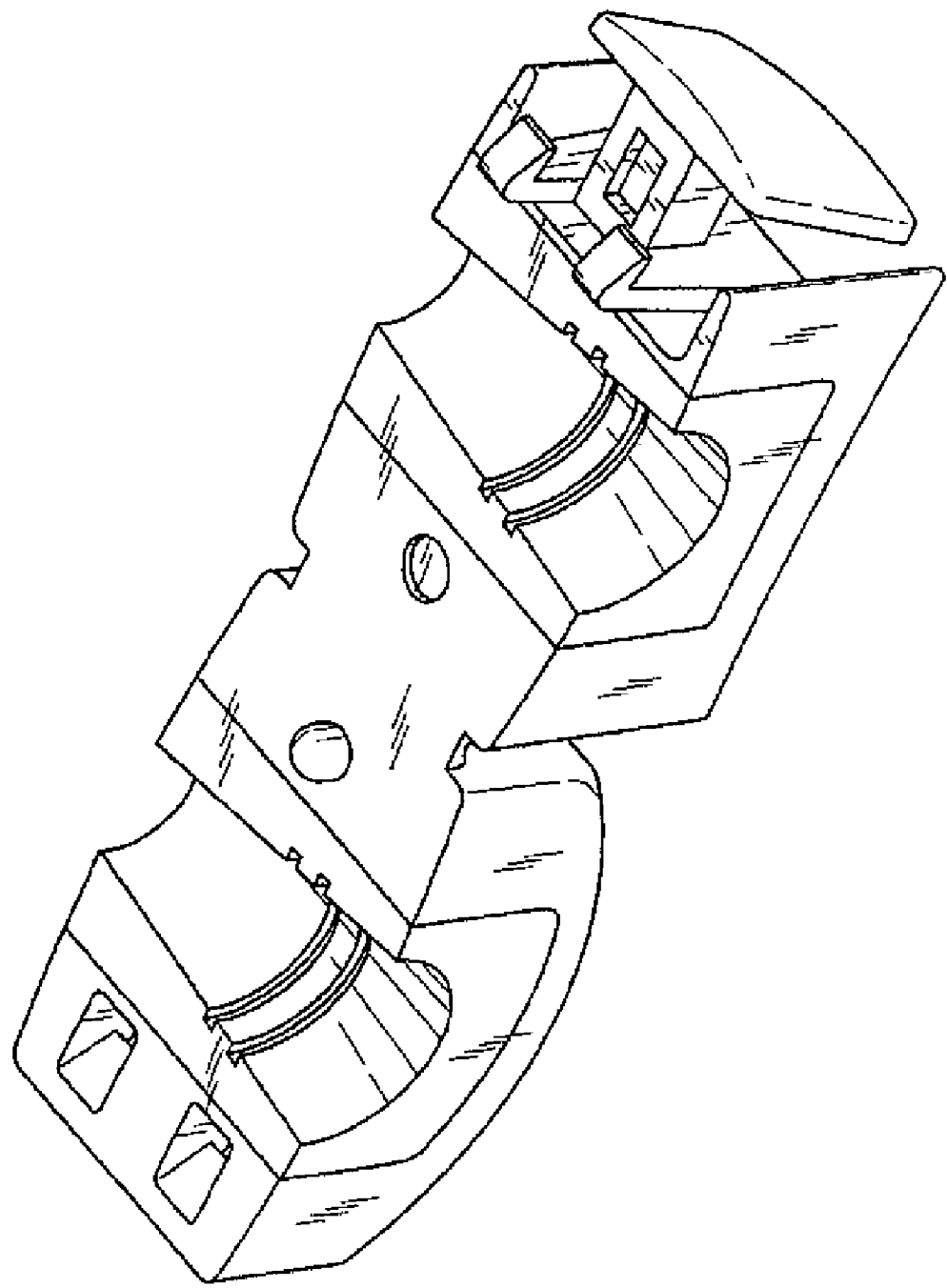
FIG. 18 illustrates a perspective view of retainer of an additional embodiment of a medical line securement device in accordance with the disclosure herein.

Furthermore, the skilled artisan will recognize the interchangeability of various features from different embodiments. For example, variations in the latch design which place the latch on the cover and the openings on the base may be combined with systems in which the projections are disposed upon the base of the retainer in order to grip the medical article even before the cover is secured in position. In another example, a slotted channel design might be used in a retainer having a compressible channel, as shown in FIG. 18. Similarly, the various aspects of the latch design, as well as other known equivalents for the described features, can be mixed and matched by one of ordinary skill in this art to produce securement devices and techniques in accordance with principles of the system described herein.

Although these techniques and systems have been disclosed in the context of certain embodiments and examples, it will be understood by those skilled in the art that these techniques and systems may be extended beyond the specifically disclosed embodiments to other alternative embodiments and/or uses and obvious modifications and equivalents thereof. Thus, it is intended that the scope of the systems disclosed herein disclosed should not be limited by the particular disclosed embodiments described above, but should be determined only by the scope of the claims that follow.

What is claimed is:

1. A securement system for securing a medical article having an elongated body and at least one outwardly extending member that extends from the elongated body, the system comprising:

a retainer comprising a body having a first portion and a second portion, the first and second portions being movable with respect to one another to establish a closed condition and an open condition, the first and second portions cooperating to form a channel at least when the retainer is in the closed condition, a radius of at least a portion of the channel being generally constant along its longitudinal length, the first portion of the body having at least two slots which extend in a direction generally normal to the axis of the channel of the retainer, at least a portion of one of the at least two slots being disposed between the first and second portions, each slot being sized to receive a portion of the at least one outwardly extending member and limit the outwardly extending member from moving in a direction generally parallel to a longitudinal axis of the retainer; and an anchoring device having a lower surface with at least a portion covered with adhesive for adhering to a patient, one of the first and second portions of the body being connected to the anchoring device through the other one of the first and second portions, wherein the outwardly extending member of the medical article abuts the at least one surface of the retainer when the retainer is in the closed condition to inhibit longitudinal motion of the medical article through the retainer in at least a longitudinal direction.

2. A securement system as in claim 1 further comprising a latch configured to secure the retainer in the closed condition.

3. A securement system as in claim 1, wherein at least a portion of the channel includes a width, as measured in a lateral direction, which tapers in size.

4. A securement system as in claim 1, wherein the slots are sized to allow the at least one outwardly extending member to at least partially rotate about the axis of the channel when the retainer is in the open condition.

5. A retainer for releasably securing a at least a portion of a medical article having an outwardly extending member with a maximum radial dimension from an axial centerline, the retainer comprising:
 a body comprising a first portion and a second portion, the first and second portions being movable with respect to one another to establish a closed configuration and an open configuration, the first portion having a first groove and the second portion having a second groove, the first and second grooves disposed so that when the first and second portions are in the closed configuration the grooves define a channel with a central axis, the channel defining at least two slots spaced from one another along the central axis and which extend in a direction generally normal to the central axis, at least a portion of one of the at least two slots being disposed between the first and second portions, each slot being sized to receive a portion of the outwardly extending member and limit the outwardly extending member from moving in a direction generally parallel to the central axis, the channel having a minimum radial dimension from an axial centerline of the channel, the minimum radial dimension of the channel being smaller than the maximum radial dimension of the outwardly extending member; and
 an anchor having a lower surface with at least a portion covered with adhesive for adhering to a patient, one of the first and second portions of the body being connected to the anchor through the other one of the first and second portions.

6. A retainer as in claim 5, wherein a radius of the channel tapers along the longitudinal length of the channel.

7. A retainer as in claim 5 wherein the radius of the channel is constant along its longitudinal length.

8. A retainer as in claim 5 further comprising a latch configured to secure the retainer in the closed configuration.

9. A retainer for releasably securing an elongated medical article having an outwardly extending member with a maximum radial dimension from an axial centerline of the elongated medical article, the retainer comprising:
 a body comprising a first portion and a second portion, the first and second portions being movable with respect to one another to establish a closed configuration and an open configuration, the first portion and the second portion defining a channel with a central axis at least when the first and second portions are in the closed configuration, each of the first and second portions having a series of grooves, the series of grooves in the first portion being disposed along the central axis and aligned with the series of grooves in the second portion so as to define two slots at least when the first and second portions are in the closed configuration, at least a portion of one of the two slots being disposed between the first and second portions, each slot being sized to receive a portion of the outwardly extending member and limit the outwardly extending member from moving in a direction generally parallel to the central axis, at least a portion of the channel extending for 360 degrees around the central axis at least when the first and second portions are in the closed configuration, the channel having a proximal end, a distal end and a minimum radial dimension from the central axis of the channel, the minimum radial dimension of the channel being smaller than the maximum radial dimension of the medical article, the first and second portions of the retainer body being configured so that at least outwardly extending member passes between the proximal and distal ends of the channel at least when the medical article is entering the channel and before the first and second portions are moved from the open configuration to the closed configuration; and
 an anchor having a lower surface with at least a portion covered with adhesive for adhering to a patient, one of the first and second portions of the body being connected to the anchor through the other one of the first and second portions.

10. A retainer as in claim 9, wherein at least a portion of the channel includes a width, as measured generally in a lateral direction, which tapers in size.

11. A retainer as in claim 9, wherein a radius of the channel tapers along the longitudinal length of the channel.

12. A retainer as in claim 9, wherein the portion of the medical article having the maximum radial dimension passes into one of the slots of the channel.

13. A retainer as in claim 9, wherein the slots are sized to allow the portion of the medical article having the maximum radial dimension to at least partially rotate about the axis of the channel when the retainer is in the open configuration.

* * * * *

UNITED STATES PATENT AND TRADEMARK OFFICE
CERTIFICATE OF CORRECTION

| | |
|---|---|
| PATENT NO. | : 7,785,295 B2 |
| APPLICATION NO. | : 11/837483 |
| DATED | : August 31, 2010 |
| INVENTOR(S) | : Steven F. Bierman |

It is certified that error appears in the above-identified patent and that said Letters Patent is hereby corrected as shown below:

At Column 1, Line 22 (Approx.), Change "escapement" to --securement--.

At Column 2, Line 10, After "retainer" insert --.--.

At Column 12, Line 38, After "embodiment" insert --,--.

At Column 19, Line 26, After "the" delete "a".

At Column 25, Line 13 (Approx.), In Claim 4, before "slots" insert --two--.

At Column 25, Line 17 (Approx.), In Claim 5, after "securing" delete "a".

Signed and Sealed this
Nineteenth Day of March, 2013

Teresa Stanek Rea
*Acting Director of the United States Patent and Trademark Office*